US009022918B2

(12) United States Patent
Chu

(10) Patent No.: US 9,022,918 B2
(45) Date of Patent: May 5, 2015

(54) SYSTEMS, DEVICES, AND METHODS FOR DELIVERING AN IMPLANT

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1524 days.

(21) Appl. No.: 11/906,967

(22) Filed: Oct. 3, 2007

(65) Prior Publication Data
US 2008/0082121 A1  Apr. 3, 2008

Related U.S. Application Data

(60) Provisional application No. 60/849,406, filed on Oct. 3, 2006.

(51) Int. Cl.
*A61F 2/02* (2006.01)
*A61F 2/00* (2006.01)
*A61B 17/062* (2006.01)
*A61B 17/04* (2006.01)
*A61B 17/28* (2006.01)
*A61B 17/00* (2006.01)
*A61B 17/29* (2006.01)

(52) U.S. Cl.
CPC ............ *A61F 2/0045* (2013.01); *A61B 17/0482* (2013.01); *A61B 17/0485* (2013.01); *A61B 17/0625* (2013.01); *A61B 17/282* (2013.01); *A61B 2017/00805* (2013.01); *A61B 2017/2837* (2013.01); *A61B 2017/2845* (2013.01); *A61B 2017/2926* (2013.01)

(58) Field of Classification Search
USPC ............... 600/29–32; 128/885; 606/144, 139, 606/151, 232
See application file for complete search history.

(56) References Cited

U.S. PATENT DOCUMENTS

| 5,871,488 | A | 2/1999 | Tovey et al. |
| 6,217,592 | B1 | 4/2001 | Freda et al. |
| 6,264,676 | B1 * | 7/2001 | Gellman et al. ............. 606/232 |
| 2003/0023250 | A1 | 1/2003 | Watschke et al. |
| 2003/0130670 | A1 | 7/2003 | Anderson et al. |
| 2003/0176762 | A1 | 9/2003 | Kammerer |
| 2004/0039453 | A1 | 2/2004 | Anderson et al. |
| 2004/0078035 | A1 | 4/2004 | Kanehira et al. |

(Continued)

FOREIGN PATENT DOCUMENTS

| EP | 0 684 012 | 12/1999 |
| WO | WO-98/19606 | 5/1998 |

(Continued)

OTHER PUBLICATIONS

Partial International Search Report from PCT/US2007/021354 dated Mar. 14, 2008.

(Continued)

*Primary Examiner* — Christine H Matthews

(57) ABSTRACT

The present disclosure provides systems, methods, devices, and kits for delivering an implant to an anatomical site in a patient. In some instances, a delivery device for delivering an implant includes a receiver with a through-lumen and a transfer pin for associating with the implant and the lumen. In some embodiments, a method for delivering an implant to an anatomical site in a patient comprises transferring the implant or a portion thereof from one section of a delivery device to another.

38 Claims, 20 Drawing Sheets

(56) References Cited

U.S. PATENT DOCUMENTS

| | | | |
|---|---|---|---|
| 2004/0144395 A1* | 7/2004 | Evans et al. | 128/885 |
| 2005/0004427 A1 | 1/2005 | Cervigni | |
| 2005/0090706 A1* | 4/2005 | Gellman et al. | 600/29 |
| 2005/0131390 A1 | 6/2005 | Heinrich et al. | |
| 2005/0177022 A1 | 8/2005 | Chu et al. | |
| 2005/0245787 A1 | 11/2005 | Cox et al. | |
| 2005/0250977 A1 | 11/2005 | Montpetit et al. | |
| 2006/0178681 A1 | 8/2006 | Kortenbach et al. | |
| 2006/0287658 A1* | 12/2006 | Mujwid et al. | 606/144 |
| 2008/0004487 A1* | 1/2008 | Haverfield | 600/30 |

FOREIGN PATENT DOCUMENTS

| | | |
|---|---|---|
| WO | WO-01/49095 | 7/2001 |
| WO | WO-2005/051204 | 6/2005 |
| WO | WO-2006/133289 | 12/2006 |

OTHER PUBLICATIONS

International Search Report from PCT/US2007/021354 dated Jul. 7, 2008.

International Preliminary Report on Patentability dated Apr. 16, 2009 from PCT/US2007/021354.

* cited by examiner

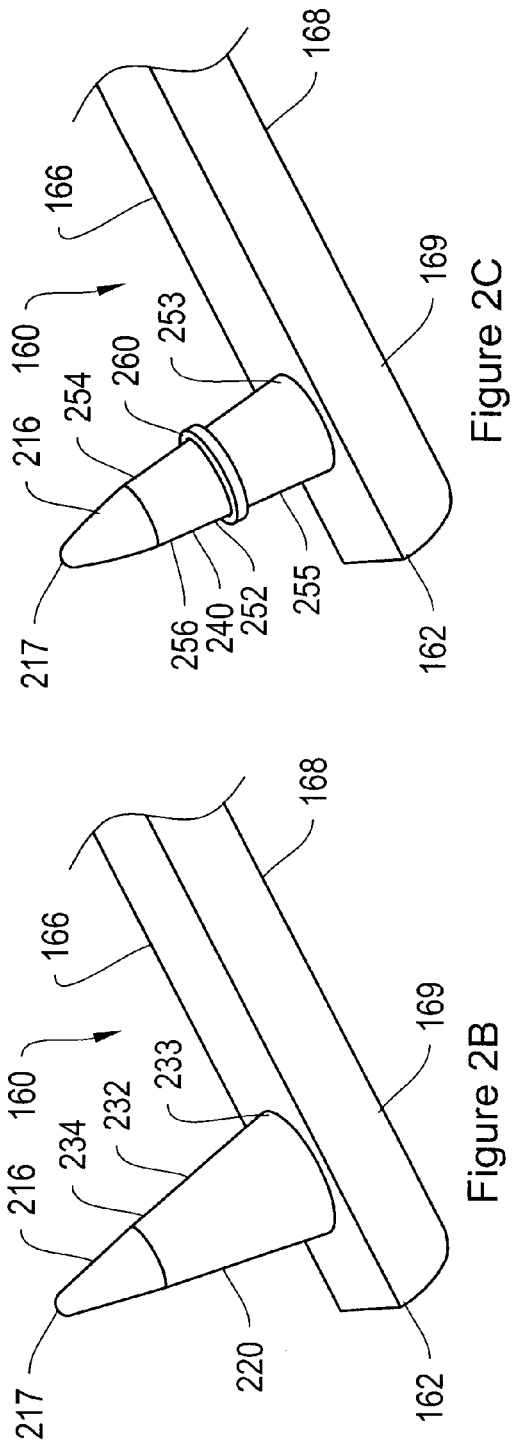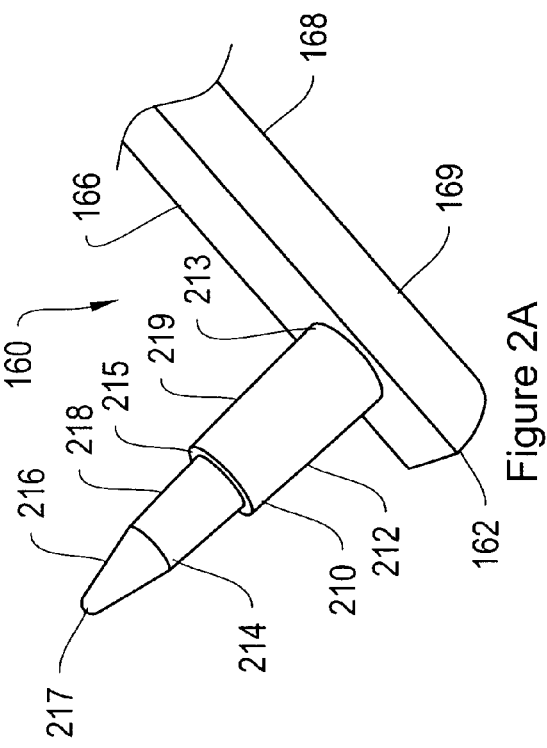
Figure 2A
Figure 2B
Figure 2C

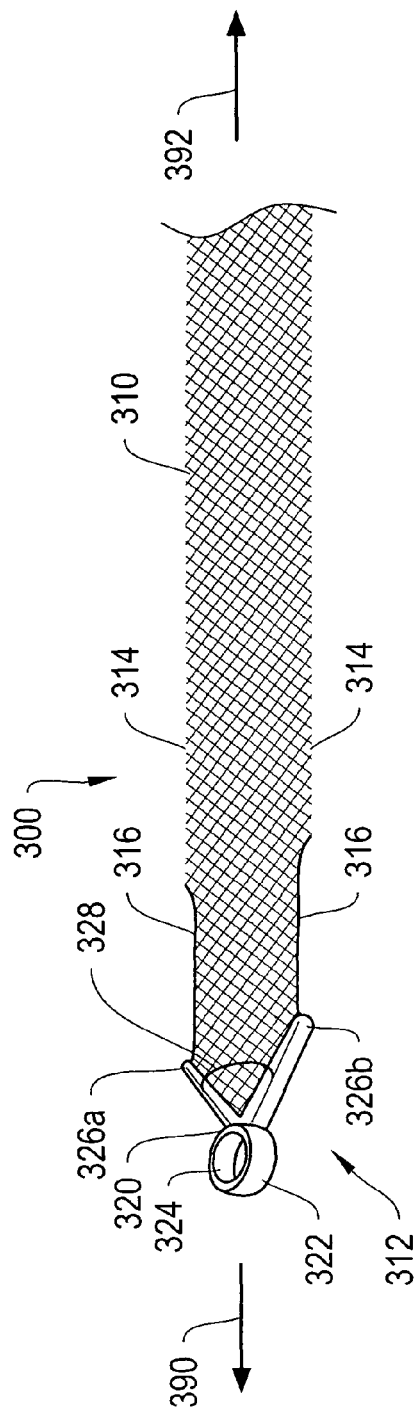
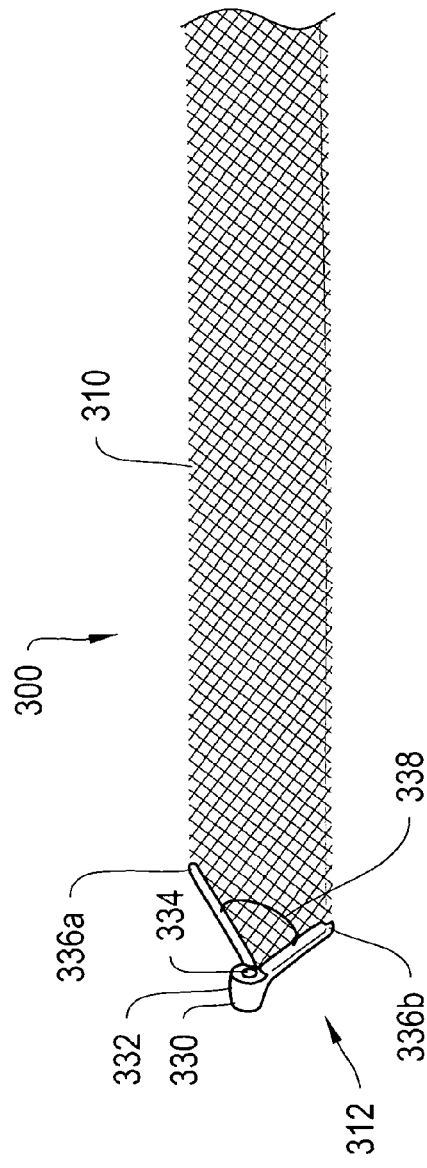

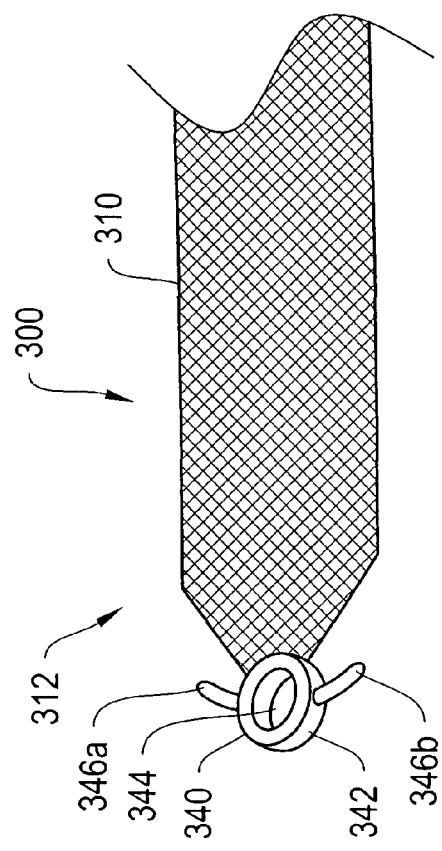
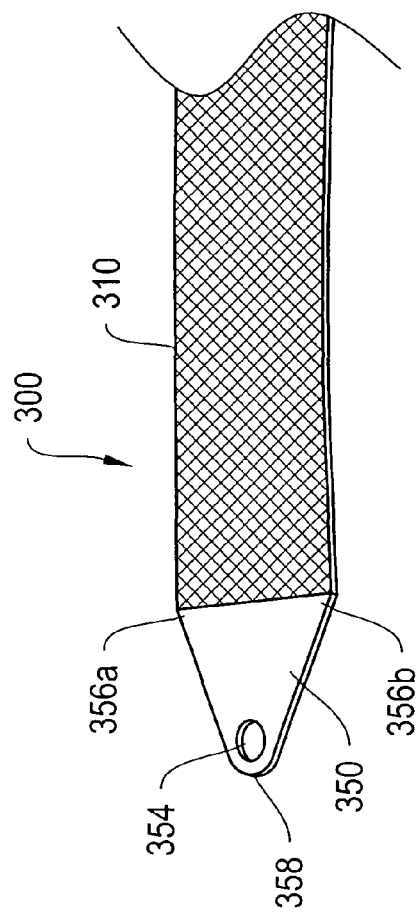

SYSTEMS, DEVICES, AND METHODS FOR DELIVERING AN IMPLANT

CROSS REFERENCE TO RELATED APPLICATIONS

This application claims the benefit of and priority to U.S. Provisional Patent Application Ser. No. 60/849,406 filed on Oct. 3, 2006, which is hereby incorporated by reference in its entirety.

FIELD OF ENDEAVOR

The present disclosure generally relates to systems, devices, and methods for delivering a supportive sling to an anatomical location in a patient. In various embodiments, the present disclosure is directed to systems, devices, and methods relating to delivery of an implant or portion thereof, such as a mesh strap and/or a sling, to an anatomical site in a patient to treat urinary incontinence.

BACKGROUND

Pelvic floor disorders afflict many men and women. According to some studies, about 1 out of 11 women needs surgery for a pelvic floor disorder during her lifetime. The pelvic floor generally includes muscles, ligaments, and tissues that collectively act to support anatomical structures of the pelvic region, including the uterus, the rectum, the bladder, and the vagina. Pelvic floor disorders include vaginal prolapse, vaginal hernia, cystocele, rectocele, and enterocele. Such disorders are characterized in that the muscles, ligaments and/or tissues are damaged, stretched, or otherwise weakened, which causes the pelvic anatomical structures to fall or shift and protrude into each other or other anatomical structures.

Moreover, pelvic floor disorders often cause or exacerbate female urinary incontinence (UI). One type of UI, called stress urinary incontinence (SUI), affects primarily women and is generally caused by two conditions—intrinsic sphincter deficiency (ISD) and hypermobility. These conditions may occur independently or in combination. In ISD, the urinary sphincter valve, located within the urethra, fails to close (or "coapt") properly, causing urine to leak out of the urethra during stressful activity. In hypermobility, the pelvic floor is distended, weakened, or damaged, resulting in increases in intra-abdominal pressure (e.g., due to sneezing, coughing, straining, etc.) and consequently the bladder neck and proximal urethra rotate and descend. As a result, the urethra does not close with sufficient response time, and urine leaks out of the urethra.

UI and pelvic floor disorders, which are usually accompanied by significant pain and discomfort, are typically treated by implanting a supportive sling in or near the pelvic floor region to support the fallen or shifted anatomical structures or to, more generally, strengthen the pelvic region by, for example, promoting tissue ingrowth. Often, treatments of stress incontinence are made without treating the pelvic floor disorders at all, potentially leading to an early recurrence of the pelvic floor disorder.

Existing devices, methods, and kits for treatment typically apply delivery devices to position a supportive sling into a desired position in the pelvic region. However, these devices may be difficult for a surgeon to manipulate within some parts of the pelvic region without adversely affecting surrounding anatomical structures during the delivery process. Moreover, when treating pelvic floor disorders and UI it is often desirable to anchor the sling to a plurality of locations in the pelvic region, but many commonly available surgical kits do not provide devices that are suitably sized, shaped, and/or convenient. Thus, surgeons have limited ability to access different locations in the pelvic region. Accordingly, medical operators and patients need improved systems, methods, devices, and surgical kits for the treatment of pelvic floor disorders and/or urinary incontinence.

SUMMARY

The present disclosure relates to systems, methods, devices, and kits for delivering and placing a medical implant at an anatomical site in the body of a patient. In some embodiments, the disclosure relates to delivery devices for delivering an implant or portion thereof, such as a mesh strap and/or a sling, to an anatomical site, such as the sacrospinous ligament or the tendinous arch of the levator ani muscle, in a patient. In certain embodiments, the delivery device comprises:

a first section including a receiver with an optional sloped surface located at a distal portion of the first section, the receiver including a through-lumen; and a second section including a transfer pin located at a distal portion of the second section, the transfer pin being adapted for associating with the implant and being movable relative to the first section;

wherein the lumen is adapted to receive the transfer pin and the implant when the transfer pin is associated with the implant.

In some instances, the lumen of the receiver is substantially cylindrical. The cross-sectional area of the lumen of the receiver may vary along a length of the lumen. In certain applications, the lumen includes a notch, such as a notch that is relatively narrow or wide with respect to the rest of the lumen. In certain embodiments, the lumen includes a first relatively narrow and a second relatively a wide notch. The lumen may extend between a first surface and a second surface of the first section, for example, along a width of the receiver or first section.

In certain aspects, the transfer pin is substantially straight and/or conical. In other aspects, the transfer pin includes at least one curved section. In some embodiments, the transfer pin includes a shaft and a terminal section including a tip. The shaft may include a relatively narrow section and a relatively wide section. In some applications, the transfer pin includes a shoulder and/or at least one projection. In certain embodiments, the terminal section is substantially conical. In some instances, the transfer pin is adapted to interfit within an aperture of an implant associator.

In certain embodiments, the device further comprises two handles that are adapted to close relative to one another to effect entry of the transfer pin into the lumen of the receiver. The device may also include a locking mechanism for releasably locking the first and second sections in at least one predetermined position relative to one another. The device may further include a separating mechanism for resiliently urging the first and second sections apart.

In some instances, at least one of the first and second sections includes at least one curved section and/or an optional stopper. In certain aspects, a pivot and/or a cam system operatively connects between the first and second sections.

In some applications, the device further comprises a shaft with distal and proximal ends, the first section and the second section being located adjacent the distal end of the shaft, and a housing located adjacent the proximal end of the shaft. The device may further include a trigger associated with, emanating from, and/or connected to the housing, the trigger being adapted to effect entry of the transfer pin into the lumen of the receiver.

The present disclosure also relates to systems for delivering an implant to an anatomical site, such as the sacrospinous ligament or the tendinous arch of the levator ani muscle, in a patient comprising:

a delivery device including first and second sections, the first section including a receiver having a through-lumen, the second section including a transfer pin; and an implant, including at least two extensions, for example, 2, 4, or 6 extensions, and a central portion for providing support to an anatomical site in a patient;

wherein the transfer pin is adapted for associating with the implant.

In some embodiments, the implant includes at least one tanged edge, at least one non-tanged edge, and/or combinations thereof. In certain instances, the implant includes an implant associator associated with at least one extension at an end thereof. The implant associator may include a ring with a lumen adapted to receive the transfer pin of the delivery device. The implant associator may also include one or more wings adapted to impede advancement, at least in one direction, of the implant associator through the lumen of the delivery device. In some instances, the implant comprises a protective pouch or envelope for completely or at least partially enclosing or covering a portion of the implant, for example a mesh strap or sling. The protective pouch or envelope may include one or more, for example two, sections or sleeves which cooperate to completely or at least partially enclose or cover a portion of the implant.

The present disclosure also relates to methods for transferring an implant, such as a mesh strap and/or sling, or portion thereof from a second section of a delivery device to a first section of the delivery device, comprising associating the implant with a transfer pin of the second section, and closing the delivery device such that that the transfer pin and associated implant passes through a lumen of the first section. In certain instances the method further comprises transferring the implant through a tissue, such as the sacrospinous ligament or the tendinous arch of the levator ani muscle, of a patient. In some applications, the implant includes an implant associator and/or a ring for associating with the transfer pin.

The present disclosure also relates to methods for securing an implant, such as a mesh strap and/or sling, or portion thereof to an anatomical site, such as the sacrospinous ligament or the tendinous arch of the levator ani muscle, in a patient, comprising:

creating an incision in the pelvic region, such as in the vaginal wall, of a patient;

associating a second section of a delivery device with the implant;

inserting the delivery device and the implant into the patient via the incision to a location near the anatomical site; and transferring the implant or a portion thereof from the second section of the delivery device, through tissue of the patient at the anatomical site, to a first section of the delivery device. In some embodiments, the implant includes an implant associator and/or a ring for associating with the second section of the delivery device.

BRIEF DESCRIPTION OF THE DRAWINGS

The following figures depict illustrative embodiments of the invention in which like reference numerals refer to like elements. These depicted embodiments may not be drawn to scale and are to be understood as illustrative of the invention and not as limiting in any way.

FIGS. 2A-C depict bottom sections of a delivery device with various types of transfer pins according to illustrative embodiments of the invention.

FIGS. 3A-D depict implants with various embodiments of implant associators according to illustrative embodiments of the invention.

ILLUSTRATIVE DESCRIPTION

Figure 1:
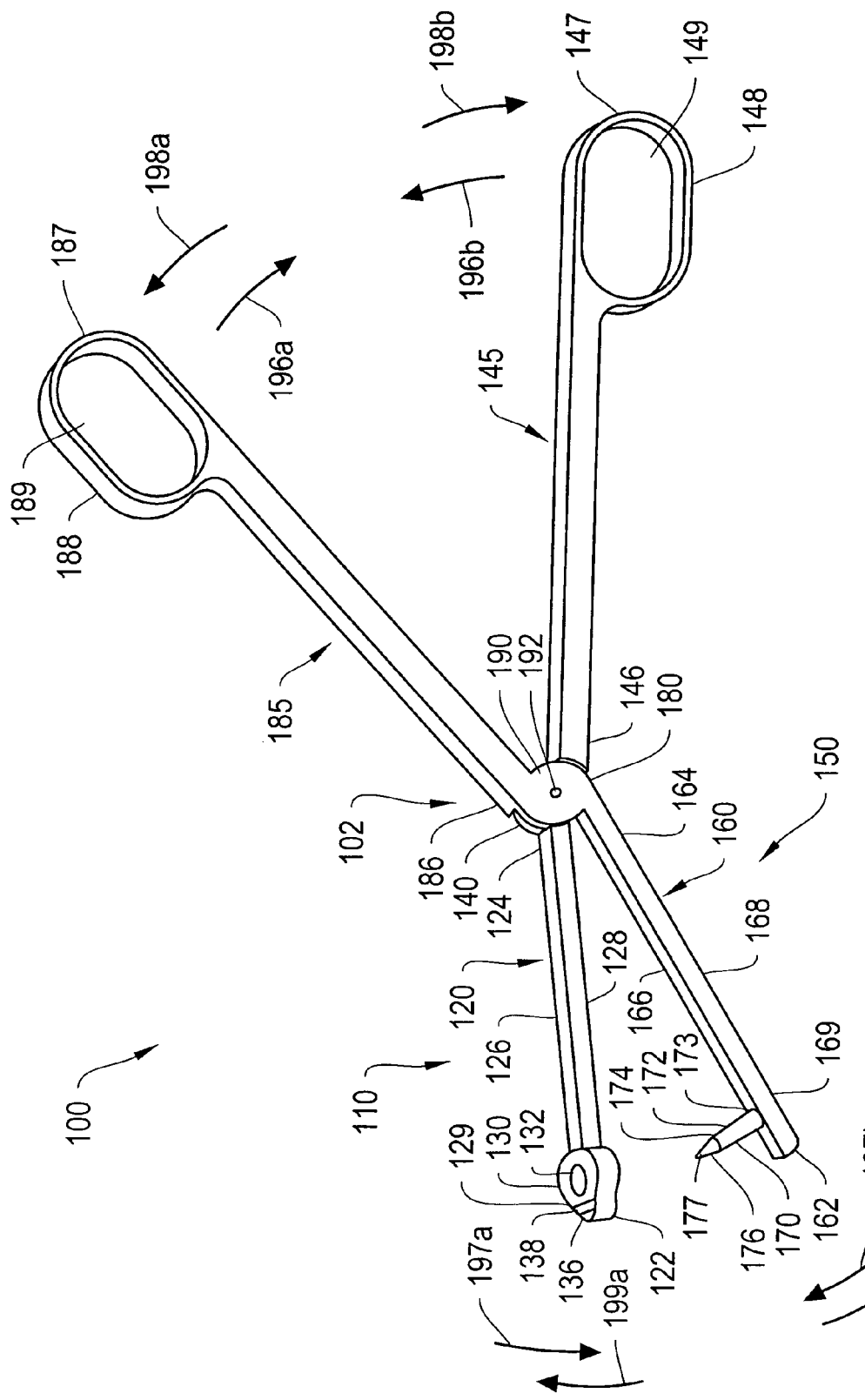
FIG. 1 depicts a delivery device according to an illustrative embodiment of the invention.

The present disclosure, in various illustrative embodiments, relates to systems, methods, devices, and kits for delivering and placing a medical implant at an anatomical site in the body of a patient. In some embodiments, the systems, methods, devices, and kits disclosed herein are useful in delivering an implant to the pelvic region of a patient for pelvic floor repair and/or for treatment of urinary incontinence. The patient may be either a female patient or a male patient, but is described below for illustrative purposes as being female. In some instances, the systems and kits include devices with features that are sized and shaped to deliver the surgical implant to the pelvic region, and surgical implants sized, shaped, and constructed to support various organs within the pelvic region, or more generally to promote tissue growth in and the general stability of the pelvic region.

In some illustrative examples, the present disclosure additionally or alternatively provides delivery devices, systems, and methods for placing an implant, such as a sling, or a portion thereof, for supporting an organ in a patient's pelvic region for treating urinary incontinence, including SUI and/or pelvic floor disorders. In certain applications, the organ includes one or more of a urethra, bladder, bladder neck, uterus, rectum, or a portion thereof. The methods include trans-vaginal approaches. In one aspect, the invention provides a delivery device for prepubicly delivering a supportive sling to the periurethral tissue of a patient, for example, under a bladder neck or mid-urethral location.

In some embodiments, the delivery device includes a transfer pin, adapted for receiving an implant or a portion thereof, and a receiver adapted for receiving the transfer pin optionally while associated with the implant. In certain embodiments, the implant includes an implant associator for associating the implant with a transfer pin, a central region, and a plurality of extensions, such as mesh straps, that extend from the central region and are adapted for securing or anchoring at respective locations in the pelvic region of a patient to appropriately position and/or tension the implant. The extensions may be anchored to the patient's pelvic floor using delivery devices that drive the extensions through the tissues, ligaments, and/or muscle regions thereof and/or transfer the implant or a portion thereof from one portion, section, region, or component of the delivery device to another. Hence, in certain embodiments, the delivery devices as described herein provide methods for transferring a portion of an implant, such as a mesh strap, from a section of the device to another section of the device. In some embodiments, the association of a portion of an implant with an anatomical site of a patient and transfer of a portion of an implant from a section of a delivery device to another section of a delivery device occur sequentially and/or simultaneously.

The delivery devices may be configured to allow the operator to deliver and secure the implant to posterior regions of the pelvic floor, such as the sacrospinous ligament and/or the tendinous arch of the levator ani muscle. Such anatomical sites are convenient locations for anchoring the straps of pelvic floor implants within the pelvic region. An operator may access these anatomical sites by guiding the devices through one or more incisions made in the pelvic region, for example, a vaginal incision made in the vaginal wall, and delivering the implant to a suitable anchoring or securing location.

Accordingly, methods for associating delivery devices with implants, methods for delivering implants to desired locations within a patient, and methods for positioning, tensioning, and/or fixating implants within a patient are described.

The delivery devices used to deliver an implant, for example, by way of various extensions, need not be the same, and in some instances, systems and surgical kits including more than one delivery device are provided. For example, U.S. application Ser. Nos. 11/429,764, 11/400,111, 11/399,913, 11/152,898, and U.S. Provisional Patent Application No. 60/849,199, filed Oct. 3, 2006, incorporated by reference herein, disclose delivery devices that may be used in combination with devices further described herein. For example, when more than one device is employed, the devices may be differently sized and shaped to facilitate delivery to certain tissue regions. Moreover, a unique device may be employed for delivery of each implant or portion thereof. Alternatively, one or more devices may be reusable, i.e., used two or more times for delivery of multiple implants or portions thereof, and optionally sterilized between uses.

Without limitation, exemplary delivery systems, devices, implants, slings, sling attachments and methodologies that may be employed in combination with the present disclosure can be found in U.S. Pat. Nos. 7,025,772; 6,991,597; 6,953,428; 6,936,052; 6,755,781; 6,752,814; 6,669,706; 6,666,817; 6,375,662; 6,042,592; 6,042,534; U.S. patent application Ser. Nos. 11/429,764; 11/400,111; 11/399,913; 11/152,898; 11/122,712; U.S. Provisional Patent Application Nos. 60/849,320 and 60/849,320, both filed Oct. 3, 2006; U.S. patent application Ser. Nos. 10/973,010; 10/957,926; 10/939,191; 10/918,123; 10/832,653; 10/774,842; 10/774,826; 10/642,397; 10/642,395; 10/642,365; 10/641,487; 10/641,376; 10/641,192; 10/641,170; 10/640,838; 10/631,364; 10/460,112; 10/093,398; 10/093,450; U.S. Provisional Patent Application Ser. Nos. 60/578,520; 60/569,300; and 60/508,600, the entire contents of all of which are incorporated herein by reference. All operative combinations between illustrative embodiments described herein and those features described in references cited herein are considered to be potentially patentable embodiments of the invention.

With reference to the Figures, FIG. 1 depicts a delivery device 100 for delivering an implant to an anatomical location in a patient according to an illustrative embodiment of the invention. The delivery device 100 includes a first section 110, comprising a top section 120, a first pivot section 140, and a bottom handle section 145. The delivery device 100 also includes a second section 150, comprising a bottom section 160, a second pivot section 180 and a top handle section 185. In operation as described in further detail below, the first section 110 and the second section 150 are movable with respect to one another and are pivotally adjoined in a scissor-like configuration to allow a medical operator to place and secure an implant within a patient. More particularly, the top section 120 includes a distal end 122 and a proximal end 124. The bottom section 160 includes a distal end 162 and a proximal end 164. The bottom handle section 145 includes a distal end 146 and a proximal end 147, and the top handle section 185 includes a distal end 186 and a proximal end 187. The top section 120 and the bottom handle section 145 associate with the first pivot section 140 at the proximal end 124 and the distal end 146, respectively. Similarly, the bottom section 160 and the top handle section 185 associate with the second pivot section 180 at the proximal end 164 and the distal end 186, respectively. Generally, the first and second sections 110 and 120 operatively associate via a pivot system 102, comprising the first and second pivot sections 140 and 150 and a pin 192. The first section 110 and the second section 150 are associated by the pin 192, located near a center portion 190 of second pivot section 180 and a center portion (not shown) of first pivot section 140. Accordingly, the pin 192 acts as a fulcrum and/or pivot position for rotation of the first section 110 and the second section 150 with respect to one another. Moreover, the pin 192 serves to couple the first and second sections 110 and 150 together.

Although certain features of the delivery device 100 are referred to as "top" and "bottom," these terms do not necessarily imply that the device can be used only in one orientation, i.e., an orientation wherein a top portion is above a bottom portion. For example, the delivery device 100 can be inverted from the illustrated embodiment of FIG. 1, or rotated 90 degrees, i.e., "sideways," or in other orientations as deemed appropriate by the medical operator.

In some embodiments, the top section 120, the first pivot section 140, and the bottom handle section 145 are a single unit. In other embodiments, one or more of the top section 120, the first pivot section 140, and the bottom handle section 145 are separate units that are associated with one another by conventional methods, for example, by being fastened, molded, bonded, tied, or adhered to one another. Similarly, in certain instances the bottom section 150, the second pivot section 180, and the top handle section 185 are a single unit, and in other embodiments the bottom section 150, the second pivot section 180, and the top handle section 185 are separate units that are associated with one another by conventional methods.

As described above, the device 100 is handheld, and as shown in FIG. 1, the bottom handle section 145 includes one or more handles 148 near the proximal end 147. Similarly, the top handle section 185 includes one or more handles 188 near the proximal end 187. The handles 148 and 188 may be sized and shaped by conventional means to allow a medical operator to grip the delivery device 100 with one or two hands. As such, the delivery device 100 may be handheld. As shown, the handles 148 and 188 include apertures 149 and 189, respectively, for receiving the fingers of the medical operator. The handles 148 and 188 may be sized and shaped differently for accepting different fingers, for example, the aperture 189 of the handle 188 may be sized and shaped for receiving a thumb of the medical operator, and the aperture 149 of the handle 148 may be sized and shape for receiving one, two, three, or four fingers of the medical operator. Accordingly, the aperture 189 may be larger or smaller than the aperture 149. In other embodiments, the handles 188 and 148 may be sized and shaped similarly such that either may accommodate a thumb or one or more fingers of a medical operator. According to this embodiment, the device 100 can be used and gripped in either the orientation shown or in an orientation inverted from that shown. In additional embodiments, the handle 148 and/or the handle 188 are each sized and shaped for gripping by the whole hand of the medical operator, for example, such that one hand of the medical operator grasps the handle 148 and the other hand of the medical operator grasps the handle 188. In certain embodiments, the handles 148 and 188 include features to facilitate gripping by a medical operator, such as ergonomically contoured surfaces, textured surfaces, coated surfaces, additional apertures, and/or combinations thereof. The apertures 149 and 189 may include contoured surfaces, textured surfaces, coated surfaces, etc. on their perimeters to facilitate grasping by the medical operator. In some embodiments, the handles 148 and 188 do not include apertures, but, for example, contoured open surfaces, such as the handle 1448 of FIG. 14.

With continued reference to FIG. 1, the bottom section 160 includes a top surface 166 and a bottom surface 168. As shown, the top surface 166 includes a transfer pin 170 located at or near a distal portion 169 or distal end 162 of the bottom section 160. The transfer pin 170 projects from the top surface 166 away from the bottom section 160. The transfer pin 170 includes a shaft 172 having a base 173, located proximal to the top surface 166, and a crest 174, located distal to the top surface 166. The transfer pin 170 further includes a terminal section 176 extending distally from the crest 174 and ending in a tip 177. As illustrated, the transfer pin 170 is substantially circular in cross-section, however, other cross-sectional shapes such as square, triangular, rectangular, oval, star-shaped, pentagonal, hexagonal, octagonal, polygonal, trapezoidal, etc. are contemplated herein. Additional features and embodiments of transfer pins are discussed below.

The bottom section 160 may also include at a distal end 162 a sloped surface (not shown), which may facilitate insertion of the bottom section into the tissues of a patient. The distal end 162 of the bottom section 160 may be sloped or narrowing in the direction of tissue penetration, i.e., toward the distal end 162 and the top surface 166. The sloping may be continuous or it may be stepwise, for example, including one or more steps, bumps, ridges, or grooves.

As illustrated, the top section 120 of first section 110 includes a top surface 126 and a bottom surface 128. In certain embodiments, the top section 120 includes a receiver 130 located at a distal portion 129 or a distal end 122 of the top section 120. The receiver 130 includes at the distal end 122 an optional sloped surface 136, which may facilitate insertion of the receiver 130 into the tissues of a patient. The receiver 130 may be sloped or narrowing in the direction of tissue penetration, i.e., toward the distal end 122 and the bottom surface 128. The sloping may be continuous or it may be stepwise, for example, including one or more steps 138, or bumps, ridges, or grooves.

As shown, the receiver 130 includes a through-lumen 132 extending along a widthwise axis of the receiver, for example, from the top surface 126 to the bottom surface 128. The lumen 132 extends along the full width or thickness of the receiver 130 and is sized and shaped to receive therein the transfer pin 170. As described in more detail below, in some instances the lumen 132 is sized and shaped to receive therein a transfer pin that is associated with an implant. The lumen 132 may have a cylindrical shape, for example, with a relatively constant diameter. Alternatively, the lumen 132 may curve, for example, forming a convex path from the perspective of the distal end 122. The lumen 132 may also become narrower or wider on progressing from the top surface 126 to the bottom surface 128. For example, the lumen 132 may increase in cross-sectional area and/or diameter on progression from the top surface 126 to the bottom surface 128, so as to facilitate receipt of a transfer pin therein from the bottom surface. In certain embodiments, the lumen 132 is circular in cross-section and has a diameter and/or area that is constant throughout or variable, for example increasing and/or decreasing one or more times along the length of the lumen. In some embodiments, the lumen has a cross-sectional shape that is not circular, for example, square, triangular, rectangular, oval, star-shaped, pentagonal, hexagonal, octagonal, polygonal, trapezoidal, etc. or other shapes or combinations of shapes as further described below.

With continued reference to FIG. 1, when in use, a medical operator can "close" the delivery device 100 by grasping the delivery device via the handles 148 and 188 and bringing the handles together, for example by pressing or squeezing, in the direction of the arrows 196a and 196b, thus causing the first and second sections 110 and 150 to pivot about the pin 192, thereby bringing the distal ends 122 and 162 or the distal portions 129 and 169 together in the direction of the arrows 197a and 197b. On closure of the delivery device 100, the transfer pin 170 enters the lumen 132 of the receiver 130 via the bottom surface 128, partially passes through the lumen, and partially exits from the top surface 126. On closure of the delivery device, the terminal section 176 may pass through the lumen 132; a portion of the shaft 172 proximal to the crest 174 may also pass through the lumen; another portion of the shaft may remain within the lumen; and another portion of the shaft proximal to the base 173 may not have entered the lumen.

A medical operator can also "open" the delivery device 100 by reversing the steps described for closing the device; that is, the operator can grasp the device 100 via the handles 148 and 188 and bring the handles apart, in the direction of the arrows 198a and 198b, thus causing the first and second sections 110 and 150 to pivot about the pin 192, thereby bringing the distal ends 122 and 162 or the distal portions 129 and 169 apart in the direction of the arrows 199a and 199b. Opening of delivery the device 100 causes the transfer pin 170 or a portion thereof to exit from the lumen 132 via the bottom surface 128, such that the last portion of the transfer pin to exit the lumen is the tip 177.

As further depicted in FIG. 1, the pivot sections 140 and 180 and the pivot pin 192 are approximately located equidistant from the distal ends 122 and 162 and from the proximal ends 147 and 187. In some embodiments, the pivot sections 140 and 180 and the pivot pin 192 may be located further toward the distal ends 122 and 162, respectively, or further toward the proximal ends 147 and 187, respectively. For example, the pivot sections 140 and 180 and the pivot pin 192 may be from about 50% to about 90%, such as from about 55%, 60%, 65%, 70%, 75%, 80%, or 85% (+/− about 2%), of the distance between a distal end and a proximal end. In other embodiments, the pivot sections 140 and 180 and the pivot pin 192 may be from about 50% to about 90%, such as from about 55%, 60%, 65%, 70%, 75%, 80%, or 85% (+/− about 2%), of the distance between a proximal end and a distal end. The different placement of the pivot sections 140 and 180 and the pivot pin 192 may be used to facilitate opening and/or closing of the delivery device 100 by the medical operator.

FIG. 2A depicts an enlarged view of a distal portion 169 of a bottom section 160 of a delivery device 100 with a transfer pin 210 projecting from the top surface 166 away from the bottom surface 168. The transfer pin 210 includes a terminal section 216 and a shaft 212, which includes a base 213 and a crest 214. Although the transfer pin 210 is illustrated as circular in cross-section, as noted above for transfer pin 170 and also for transfer pins generally disclosed herein, other shapes are contemplated. The shaft 212 has a narrow section 218 and a wide section 219, wherein the narrow section has one or more cross-sectional dimensions smaller than one or more cross-sectional dimensions of the wide section. For example, as illustrated, the diameter of the narrow section 218 is smaller than that of the wide section 219. Accordingly, in some embodiments, the narrow section 218 and the wide section 219 meet at the shoulder 215, which is a circular step where the diameter of the shaft 212 increases on transitioning from the narrow section to the wide section. Although in the illustrated embodiment, the shoulder 215 includes an abrupt decrease in diameter in progressing from the wide section 219 to the narrow section 218, in other embodiments, the increase in decrease may be gradual or stepwise, giving rise to a shoulder that is a transitional sloped section or to more than one shoulder, respectively. The narrow section 218 and the wide section 219 may have constant diameters and/or thicknesses or they may increase or decrease in diameter on distal progression from the top surface 166. The terminal section 216 includes a tip 217 which is distal from the top surface 166. Although in the illustrated embodiment, terminal section 216 is conical in shape, the terminal section may assume other shapes suitable for penetrating one or more forms of tissue, such as contractile tissue, epithelium, muscle, ligament, and/or connective tissue. For example, the terminal section 216 may be pyramidal, star-shaped, screw-shaped, etc. The tip 217 may be blunt for blunt dissection of soft tissue, or the tip may be sharp for penetration of tissue resistant to blunt dissection.

FIG. 2B depicts an enlarged view of a transfer pin 220 on a distal portion 169 of a bottom section 160 of a delivery device 100 according to another embodiment of the invention. The transfer pin 220 includes a shaft 232 and a terminal section 216. Although the transfer pin 220 is illustrated as circular in cross-section, as noted above for other transfer pins, other shapes are contemplated. The shaft 232 includes a base 233, proximal to the top surface 166, and a crest 234, distal to the top surface. In the illustrated embodiment, the cross-sectional diameter of the shaft 232 decreases on distal progression from the base 233 to the crest 234. In other embodiments, the cross-sectional diameter of the shaft 232 is relatively constant on distal progression from the base 233 to the crest 234, for example, as shown for the shaft 172 in FIG. 1.

FIG. 2C depicts an enlarged view of a transfer pin 240 on a distal portion 169 of a bottom section 160 of a delivery device 100 according to another embodiment of the invention. The transfer pin 240 includes a shaft 252 and a terminal section 216. Although the transfer pin 240 is illustrated as circular in cross-section, as noted above for other transfer pins, other shapes are contemplated. The shaft 252 includes a base 253 proximal to the top surface 166 and a crest 254 distal to the top surface. The shaft 252 further includes a projection 260 which radially projects from the shaft 252. As illustrated, the projection 260 is circular and defines a proximal portion 255 and a distal portion 256 of the shaft 252, wherein the proximal portion is proximal to the top surface 166, and the distal portion is distal to the top surface 166. In preferred embodiments, the circular projection 260 has an external diameter greater than that of any cross-sectional portion of the distal portion 256. The circular projection 260 may have a larger or smaller diameter than one or more cross-sectional portions of proximal portion 255. In some embodiments, the projection 260 has other shapes, such as square, triangular, rectangular, oval, star-shaped, pentagonal, hexagonal, octagonal, polygonal, trapezoidal, etc. The shaft 252 may also include more than one projection. In some embodiments, the projection 260 includes bumps, nubs, spikes, etc. In the illustrated embodiment, the cross-sectional diameter of the shaft 252 is relatively constant on distal progression from the base 253 to the crest 254 with the exclusion of the projection 260. In other embodiments, the cross-sectional diameter of the shaft 252 may decrease on distal progression from the base 253 to the crest 254.

Figure 3E:
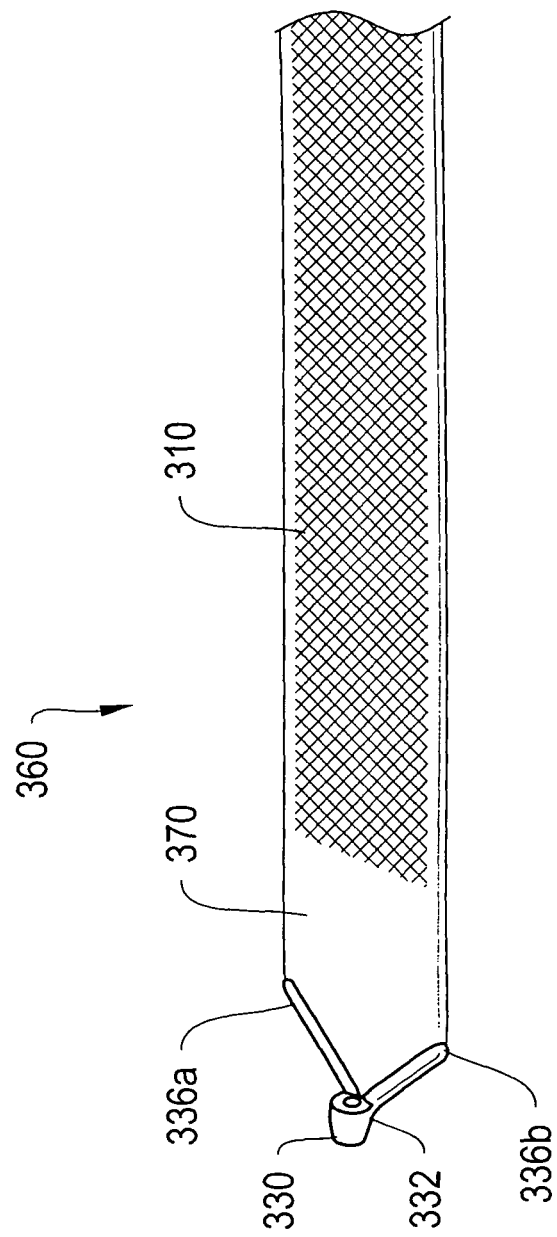
FIG. 3E depicts an implant, including an envelope with a mesh strap or sling enclosed or at least partially enclosed therein, with an implant associator.

FIG. 3A depicts a portion of an implant 300 according to an illustrative embodiment of the invention. The implant may be a sling or supportive mesh for treating pelvic floor disorders, urinary incontinence, or other disorders where support of an organ can provide treatment. The implant 300 includes an extension 310 which is a mesh strap and/or end portion of a sling that terminates in a distal portion 312. One or more portions of the mesh strap 310 may have tanged edges 314; that is, edges that have barbs, frayed sections, or other rough or sharp features. One or more portions of the mesh strap 310 may also have non-tanged or de-tanged edges 316; that is, edges that are smoothed, curved, or rounded. In certain embodiments, the mesh strap 310 includes one or more tanged edges at the distal portion 312, for example, to secure the strap within the tissue and/or to encourage tissue growth on, over, and/or through, the strap. In other embodiments, the mesh strap 310 includes one or more non-tanged edges or a combination of tanged and non-tanged edges at the distal portion 312, for example, to facilitate passage of the strap through the tissue. Other examples of tanged and non-tanged implant features are disclosed in U.S. Pat. No. 6,953,428, incorporated by reference herein, and are contemplated within the present disclosure.

In some embodiments, the distal portion 312 includes an implant associator 320, which may associate with a transfer pin such as those described herein. The implant associator 320 includes a circular ring 322 with a through aperture or lumen 324 adapted, i.e., sized and shaped, for receiving a transfer pin. Although embodiments depicted in FIG. 3A and other Figures herein include rings, such as 322, with circular apertures, such as 324, apertures of other shapes are contemplated, for example, square, triangular, rectangular, oval, star-shaped, pentagonal, hexagonal, octagonal, polygonal, trapezoidal, etc., particularly if such shapes are complementary with the shape of a corresponding transfer pin. The implant associator may be fixedly associated with the implant, for example, by heat bonding, gluing, tying, suturing, molding, etc. The implant associator may also be reversibly associated with the implant, for example, through reversible fasteners, clips, snaps, clamps, etc. As described in U.S. application Ser. Nos. 11/152,898; 11/400,111; 11/399,913, which are incorporated by reference herein, the implant associator may comprise two or more components which snap or fasten together, optionally reversibly, and sandwich or trap a portion of the implant, extension, or mesh strap therebetween, thereby associating the implant to the implant associator.

The illustrated implant associator 320 further includes two wings 326a and 326b that extend from the ring 322, for example, by projecting radially or substantially radially from the ring. In some instances the wings 326a and 326b define an angle 328. The angle 328 is preferably less than about 180 degrees, for example, from about 180 degrees to about 5 degrees. In some instances, the angle is less than about 150, 120, 110, 100, 90, 80, 70, or 60 degrees. The wings 326a and 326b define a convex shape in the direction of the arrow 390 and a concave shape in the direction of the arrow 392. The implant associator 320, and other implant associators described herein, are preferably made from a flexible material, such as a plastic or polymer, so that the angle 328 can be increased or decreased by applying appropriate external mechanical force to flex or bend wings 326a and 326b.

In operation, mesh strap 310 is inserted into the tissues of a patient in the direction of the arrow 390, i.e., in the convex direction regarding the wings 326a and 326b. The convex shape formed by the wings 326a and 326b facilitates implantation of the implant 300 into tissue such that when the wings contact tissue during implantation the wings may flex or bend, at least temporarily, so as to reduce angle 328, thereby facilitating passage of the implant associator 320 through tissue. Conversely, any retrograde movement of the mesh strap 310 in the direction of the arrow 392, i.e., in the concave direction regarding the wings 326a and 326b, is discouraged by the concave shape of the wings such that the wings can contact or abut tissue and flex or bend, at least temporarily, so as to increase angle 328, thus further impeding movement. Hence, the wings 326a and 326b serve to facilitate movement of the mesh strap 310 in the direction of the arrow 390 but to impede movement of the strap in the direction of the arrow 392.

Moreover, in the illustrated embodiment of FIG. 3A, the plane containing the circumference of the aperture 324 and the plane containing the wings 326a and 326b are approximately in the same plane and/or lie in parallel or substantially parallel plains; however, in some embodiments the circumference of the aperture and the wings lie in different planes. For example, the implant associator 320 may be flexible such that the wings 326a and 326b can bend out of the plane containing the ring 322. In some embodiments, rings described herein, such as 322, are flexible and can bend to form different shapes. The implant associators described herein, such as 320, may be associated with the mesh strap 310, for example at wings, by molding, gluing, heat bonding, or other association methods.

FIG. 3B depicts a portion of the implant 300 and mesh strap 310 with an implant associator 330 according to another illustrative embodiment of the invention. The implant associator 330 includes a ring 332 with a through aperture 334 sized and shaped for receiving a transfer pin such as those described herein. The implant associator 330 further includes two wings 336a and 336b that define an angle 338. The angle 338 is preferably less than about 180 degrees, for example, as described herein for other angles defined by wings. Moreover, in the illustrated embodiment, the plane containing the circumference of the aperture 334 and the plane containing the wings 336a and 336b do not lie in the same plane. In some embodiments, the plane containing the circumference of aperture 334 and the plane containing wings 336a and 336b are perpendicular or substantially perpendicular. In some embodiments, the plane containing the circumference of aperture 334 and the plane containing wings 336a and 336b form an angle between about 180 degrees and about 80 degrees, for example between about 170, 150, 130, or 110 degrees and about 90 degrees.

FIG. 3C depicts a portion of the implant 300 and mesh strap 310 with an implant associator 340 according to another illustrative embodiment of the invention. The implant associator 340 includes a ring 342 with a through aperture 344 sized and shaped for receiving a transfer pin such as those described herein. The implant associator 340 may be associated with the mesh strap 310 at the ring 342 by molding, gluing, heat bonding, or other association methods. The implant associator 340 optionally includes two wings 346a and 346b with features similar to those described herein for other wings.

FIG. 3D depicts a portion of the implant 300 and mesh strap 310 with an implant associator 350 according to another illustrative embodiment of the invention. The implant associator 350 includes a through aperture 354 sized and shaped for receiving a transfer pin such as those described herein. The implant associator further includes a distal tip 358 and wings 356a and 356b. Although in FIG. 3D the implant associator 350 is depicted as triangular in shape, it may have other shapes such as circular, square, rectangular, oval, star-shaped, pentagonal, hexagonal, octagonal, polygonal, trapezoidal, etc.

Although in the embodiments depicted in FIGS. 3A-D, the implant associator is depicted as associating directly with the mesh strap, in certain embodiments, this is not the case. For example, in some instances, the implant includes a protective pouch, envelope, or sleeve enclosing, either completely or at least partially, the mesh strap or sling, and the implant associator is associated with the protective envelope. FIG. 3E depicts an implant 360 including an envelope 370 with a mesh strap or sling 310 enclosed or at least partially enclosed therein. An implant associator 330 is associated with the envelope 370 at the wings 336a and 336b and optionally at the ring 332 by molding, gluing, heat bonding, or other association methods. Although FIG. 3E depicts the implant associator 330 in combination with the protective envelope 370, other implant associators as described herein may also be employed with the envelope 370. Additionally, any type of mesh strap and/or sling may be used in conjunction with the envelope. U.S. patent application Ser. No. 11/122,712 is incorporated by reference herein and describes additional sling and envelope combinations and methods which may be used with the systems, devices, and methods described herein. For instance, following delivery of the implant to an anatomical site in a patient, the envelope can be removed, thereby exposing the mesh strap or sling.

Figure 4:
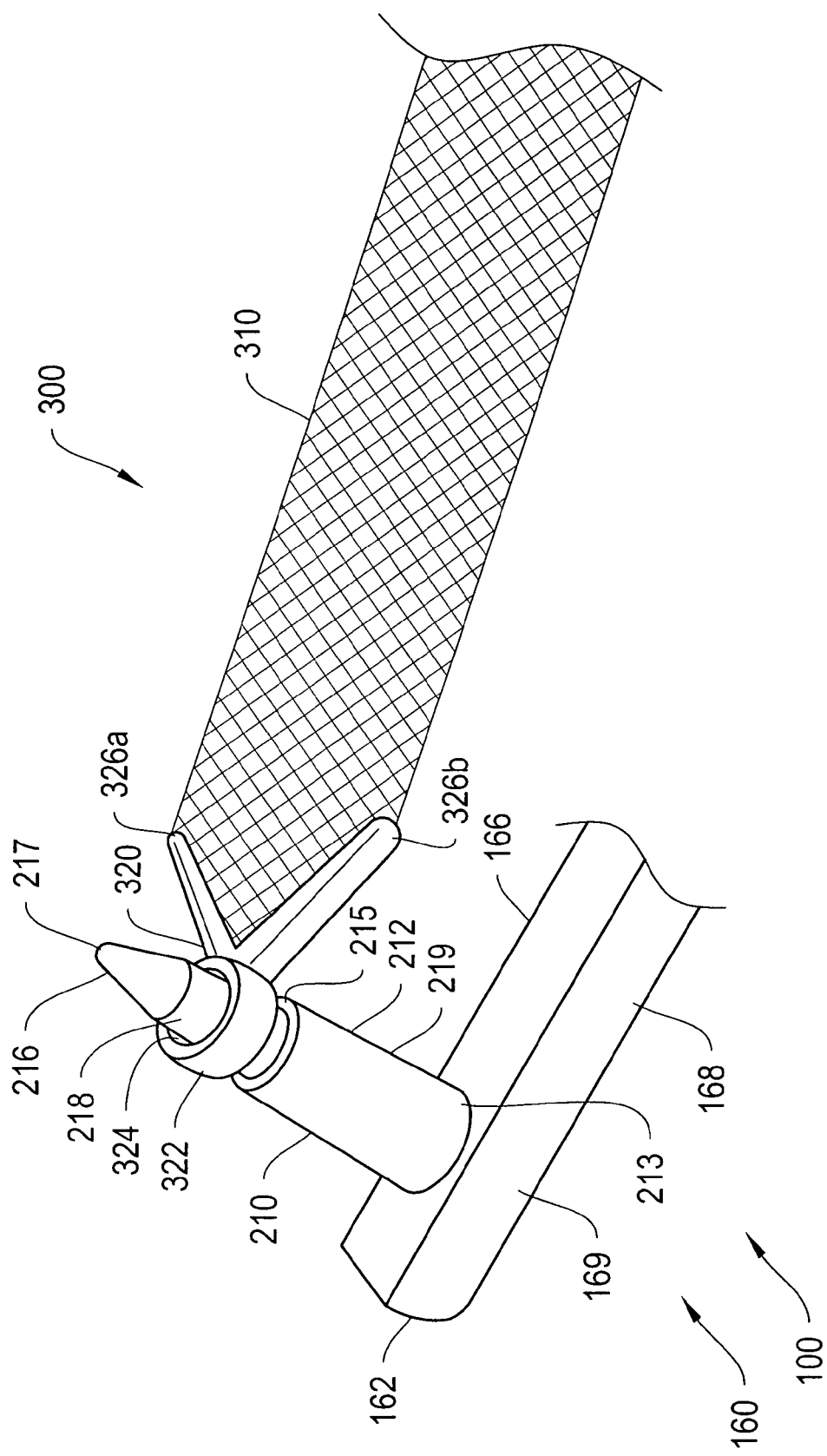
FIG. 4 depicts an implant associated with a transfer pin of a delivery device according to an illustrative embodiment of the invention.

FIG. 4 depicts a distal portion 169 of a bottom section 160 of the delivery device 100 similar to that of FIG. 2A associated with an implant 300 similar to that of FIG. 3A. As shown, the implant associator 320 is adapted to receive the transfer pin 210 within the aperture 324 of the ring 322. Preferably, the clearance between the ring 322 and the transfer pin 210 is less than about 0.5 millimeters, such as less than about 0.2, 0.1, 0.05, 0.025, or 0.01 millimeters. In preferred embodiments, the transfer pin 210 associates with the ring 322 when the terminal section 216 passes through the aperture 324 of the ring followed by a portion of the narrow section 218 of the shaft 212. The ring 322, the aperture 324, and the shaft 212 are preferably sized and shaped such that the ring and the aperture cannot advance along the shaft over shoulder 215. Thus, as the ring 322 advances along the shaft 212 toward the base 213, it reaches the shoulder 215 and the shoulder and ring abut one another preventing further progress of the ring along the shaft.

When the delivery device 100 is equipped with a transfer pin 220 similar to that shown in FIG. 2B, the shaft 232 is preferably sized and shaped such that the ring 322 and the aperture 324 cannot advance along the shaft to the base 233. In some embodiments, the cross-sectional diameter of the shaft 232 increases on progression from the crest 234 to the base 233 such that in the vicinity of the crest, the cross-sectional diameter is small enough to pass through the aperture 324 of the ring 322, and the ring can advance onto the shaft toward the base; yet as the cross-sectional diameter of the shaft increases, it eventually exceeds the internal diameter of the ring or aperture preventing further advancement of the ring along the shaft toward the base. Hence, at the point where the cross-sectional diameter of the shaft 232 begins to exceed the diameter of the aperture 324 of the ring 322, the ring will abut the shaft, preventing advancement.

Similarly, when the delivery device 100 is equipped with a transfer pin 240 similar to that shown in FIG. 2C, the shaft 252 is preferably sized and shaped such that the ring 322 and the aperture 324 can advance along the shaft toward the base 253, until reaching the circular projection 260. The circular projection 260 preferably has an external diameter larger than the inner diameter of the aperture 324 such that the ring 322 cannot pass over the projection and cannot advance further toward the base 253.

Figure 5:
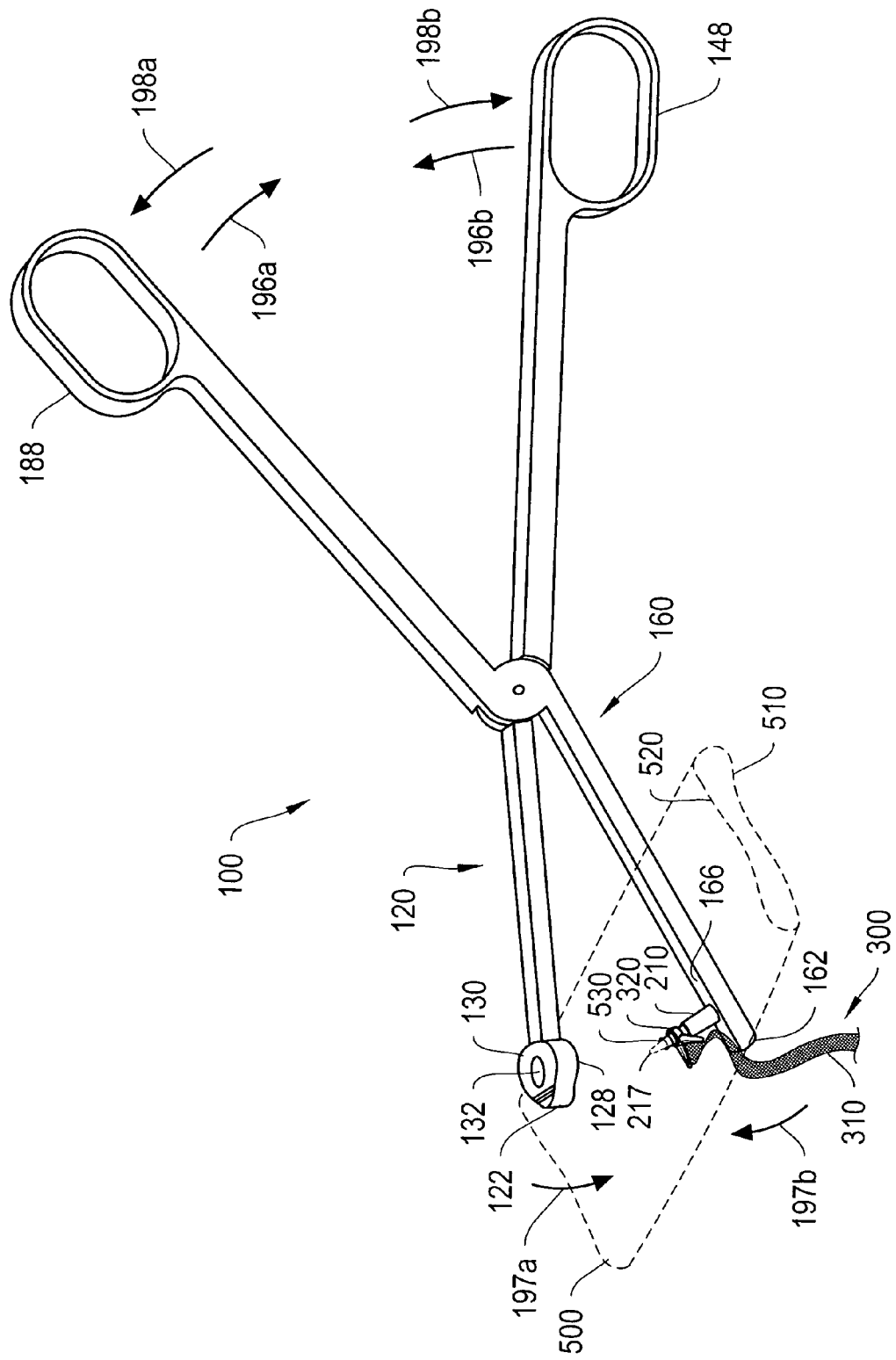
FIG. 5 depicts a delivery device associated with an implant penetrating a tissue according to an illustrative embodiment of the invention.

FIG. 5 depicts a delivery device 100 associated with an implant 300, in the process of penetrating a tissue 500. The delivery device 100 is associated with the implant 300 via the transfer pin 210 and the implant associator 320. In operation, a medical operator places the top section 120 and the bottom section 160 around the tissue 500 and closes the delivery device 100 by grasping the device by the handles 148 and 188 and squeezing the handles together in the direction of the arrows 196a and 196b. Closing the delivery device 100 causes the distal ends 122 and 162 and/or the distal portions 129 and 169 to come together in the direction of the arrows 197a and 197b, resulting in grasping of the tissue 500 by contact of the tip 217 with a bottom tissue surface 510 and contact of the receiver 130 with a top tissue surface 520. The receiver 130 may optionally include one or more surface features (not shown), such as bumps, ridges, grooves, spikes, or other textured surfaces on the bottom surface 128 and/or on the top surface 166 to improve the grip of the tissue 500. Continued closure of the delivery device 100 effects penetration of the tissue 500 by the tip 217, thus creating an incision 530. As closing continues, the transfer pin 210 further penetrates the tissue 500 at the incision 530, eventually penetrating the top tissue surface 520 and entering the lumen 132 of the receiver 130 from the bottom surface 128. As the transfer pin 210 penetrates the tissue 500 and enters the lumen 132, the implant associator 320 is also drawn into the tissue via incision 530, out of the top tissue surface 520, and into the lumen 132 of the receiver 130. The flexibility of the implant associator 320 and the wings 326a and 326b facilitate penetration into and through the tissue 500 and into and through the lumen 132 of the receiver 130.

Figure 6:
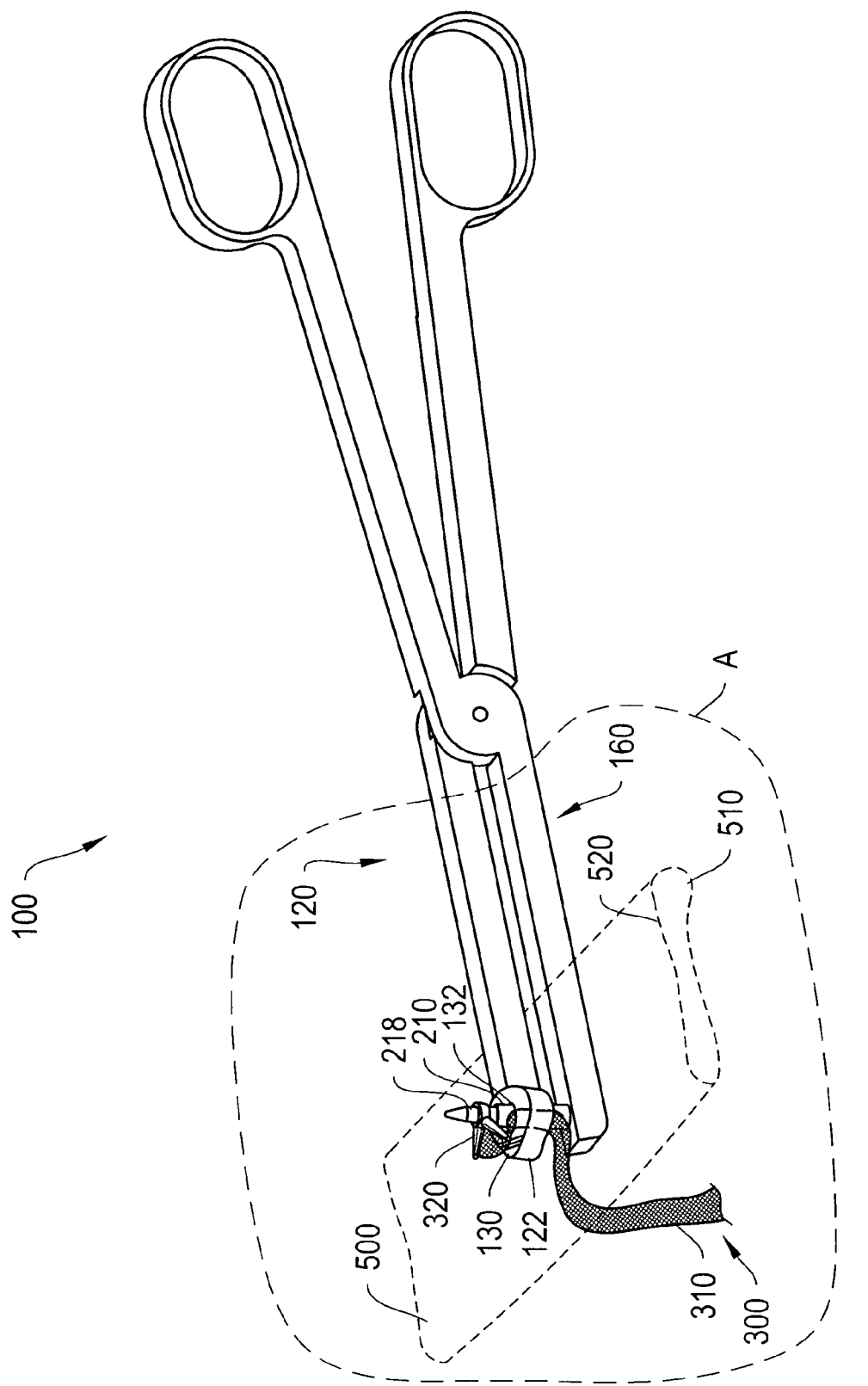
FIG. 6 depicts a transfer pin having transferred an implant through tissue to the receiver of a delivery device according to an illustrative embodiment of the invention.

FIG. 6 depicts the delivery device 100 of FIG. 5 in a closed position. In the closed position, portions of the transfer pin 210 have passed through the tissue 500 and through the lumen 132 of the receiver 130. Additionally, the implant associator 320 has also advanced through the tissue 500 and through the lumen 132 along with a portion of mesh strap 310.

Figure 7:
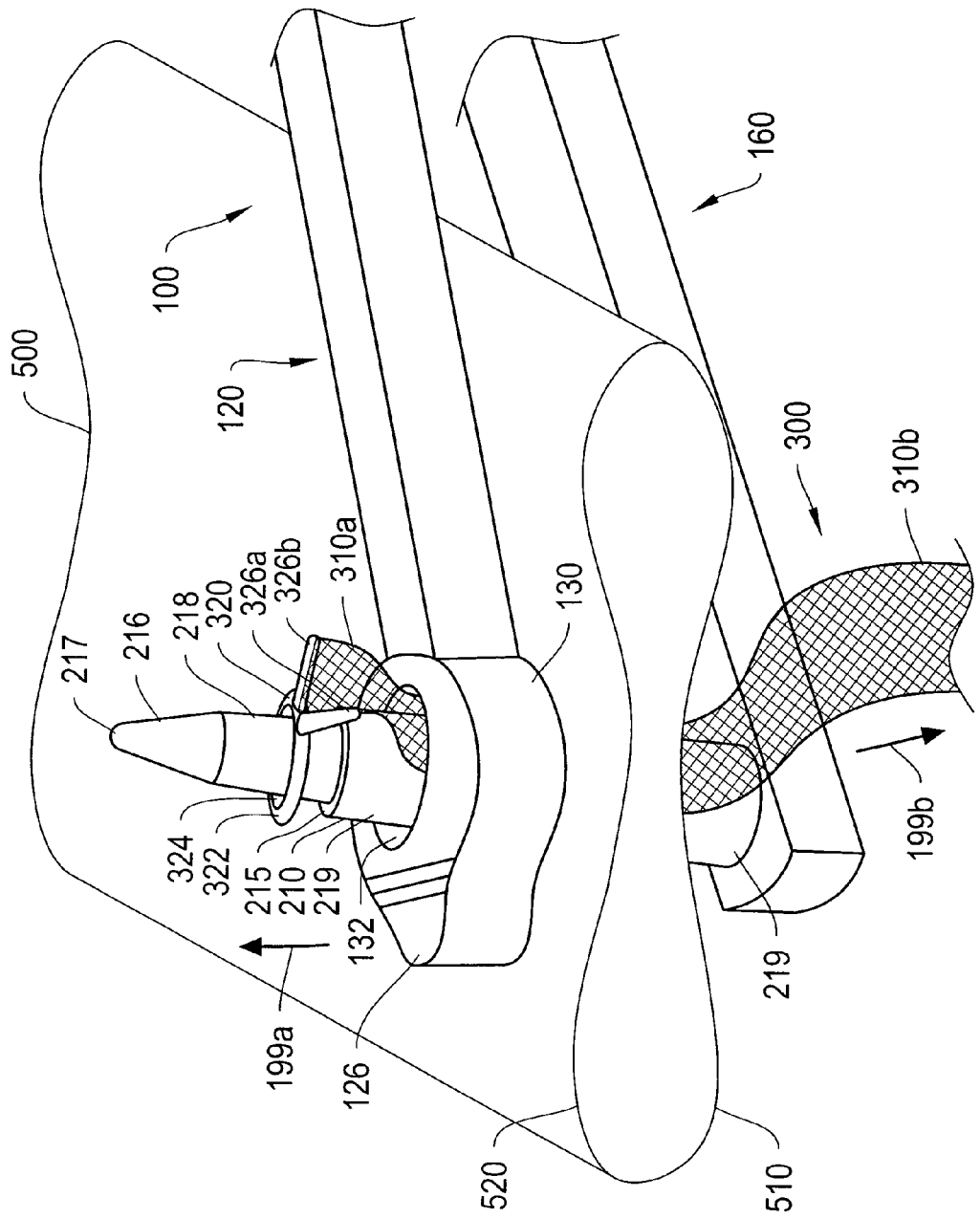
FIG. 7 depicts an enlarged view of a transfer pin having transferred an implant through tissue to the receiver of a delivery device according to an illustrative embodiment of the invention.

FIG. 7 depicts an enlarged view of the portion of FIG. 6 within the region surrounded by the dotted line A. As shown, the delivery device 100 is in the closed position and the terminal section 216, the narrow section 218, and a portion of the wide section 219 of the transfer pin 210 have penetrated through the tissue 500 and passed through the lumen 132 of the receiver 130. Additionally, the implant associator 320 has also advanced through the tissue 500 and through the lumen 132 along with a portion of mesh strap 310a, while a portion of the mesh strap 310b has not entered the tissue or the lumen. The implant associator 320, including the ring 322 and the wings 326a and 326b, are flexible such that when sufficient force is provided by the medical operator to close the delivery device 100, the implant associator may flex, bend, and/or deform, at least temporarily, to facilitate passage through the tissue 500 and through the lumen 132 of the receiver 130. Moreover, during advancement of the implant associator 320 through the tissue 500 and through the lumen 132, the wings 326a and 326b form a convex shape relative to the direction of advancement and flex, bend, contort, and/or deform as necessary. The implant associator 320 can thus collapse and/or deform in shape to facilitate passage through the tissue 500 and the lumen 132 and resume or expand to the original shape after passing through the tissue and the lumen.

As detailed above, a portion of the transfer pin 210 may be driven through the tissue 500 by closing of the delivery device 100. Alternatively, the medical operator may drive a portion of the transfer pin 210 through the tissue 500 by proper application of pressure and torque on the delivery device 100 and/or the bottom section 160 while the delivery device remains in the open or partially open position. Accordingly, in some instances, the medical operator drives the transfer pin 210 and implant associator 320 through the tissue 500 while the delivery device 100 is in the open position. Once a portion of the transfer pin 210 and the implant associator 320 have penetrated through the top tissue surface 520, the medical operator may then close the delivery device 100 to transfer the implant associator and mesh strap 310 from the transfer pin and bottom section 160 to the receiver 130 and top section 120 of the delivery device.

With continued reference to FIG. 7, once, the implant associator 320 has been advanced to the top surface 126 of the receiver 130, the transfer pin 210 may be withdrawn from the lumen 132 of the receiver by opening of the delivery device 100. Referring to FIG. 5, the medical operator may separate the handles 148 and 188 in the direction of the arrows 198a and 198b, thereby causing the receiver 130 and the transfer pin 210, depicted in FIG. 7, to move in the direction of the arrows 199a and 199b, respectively. As the transfer pin 210 is withdrawn back through the lumen 132, the implant associator 320 abuts the top surface 126 of the receiver 130 in one or more places, for example, at the projecting wings 326a and 326b, thereby preventing retrograde movement of the implant associator back through the lumen and the tissue 500. As a result, on opening of the delivery device 100, the transfer pin 210 withdraws from the aperture 324 of the ring 322, and the implant associator 320 remains on the top surface 126 of the receiver 130, while the transfer pin is further withdrawn from the lumen 132 and the tissue 500. Thus, opening of the delivery device 100 disassociates the implant associator 320 from the transfer pin 210 and the bottom section 160. Accordingly, the closing and opening of the delivery device 100 described above transfers the implant associator 320 and a portion of the mesh strap 310 from the bottom section 160 of the delivery device to the top section 120.

In alternate embodiments, the medical operator may disassociate the implant associator 320 from the transfer pin 210 by grasping the implant associator with fingers, tongs, tweezers, or forceps, and pulling in the direction of the arrow 199a. The medical operator may also disassociate the implant associator 320 from the transfer pin 210 by similarly grasping the bottom section 160 and pulling in the direction of the arrow 199b.

Figure 8:
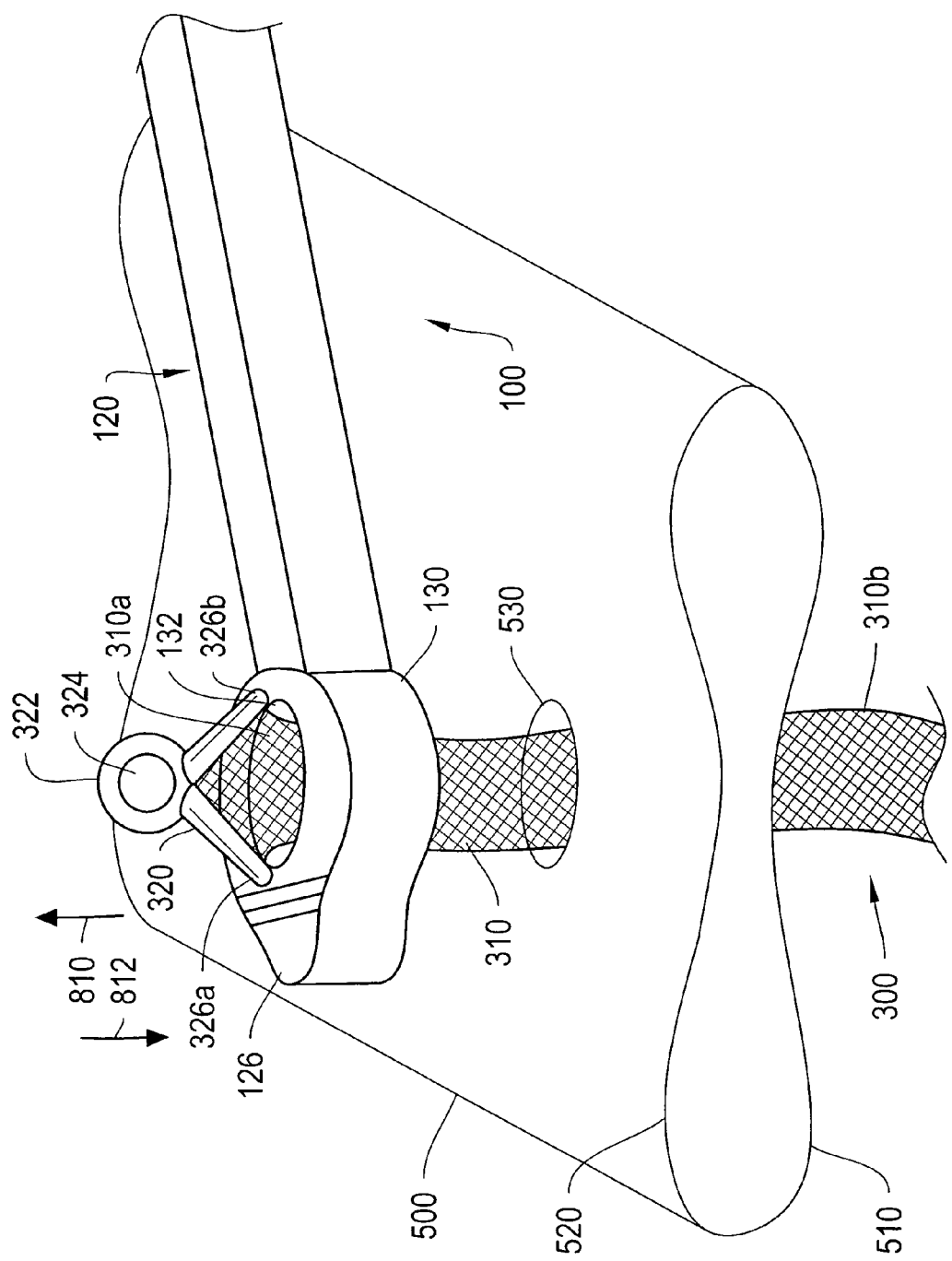
FIG. 8 depicts an implant having been transferred to the receiver of a delivery device following removal of the transfer pin according to an illustrative embodiment of the invention.

FIG. 8 depicts a portion of the implant 300 having been transferred to the top section 120 of the delivery device 100 after opening of the delivery device. With the transfer pin (not shown) withdrawn from the aperture 324 of the ring 322, from the lumen 132 of the receiver 130, and from the incision 530 of the tissue 500, the implant associator 320 remains associated with the top section 120. The medical operator may adjust the tension, positioning, etc. of the implant 300 by pulling on the mesh strap 310 by pulling the top section 120 and/or receiver 130 of the delivery device 100. The implant associator 320 and the wings 326a and 326b are preferably sized and shaped such that their maximum width and/or wingspan is larger than the diameter of the lumen 132. As such, pulling on the top section 120 and/or the receiver 130 in the direction of the arrow 810 leads to abutment of the wings 326a and 326b, due to their concave shape, with the top surface 126. This abutment prevents the implant associator 320 and the sling portion 310a from passing through the lumen 132 and back into the tissue 500. The medical operator may pull more of the mesh strap 310 through the tissue 500 if desired.

In some embodiments, the medical operator pulls on the receiver 130 to tension or position the mesh strap 310. The medical operator may also grasp the mesh strap 310 with fingers, tongs, tweezers, or forceps, for example, at the implant associator 320, and tension or position the mesh strap, for example, by pulling away from the tissue 500, such as in the direction of the arrow 810. To remove the implant associator 320 from the receiver 130, the medical operator may cut the mesh strap 310 at a location on either side of the receiver, for example, at a portion of the mesh strap just above the top tissue surface 520. The medical operator may also manually reduce the angle 328 between the flexible wings 326a and 326b thereby reducing the maximum width or wingspan of the implant associator 320 enough for the implant associator to fit back through the lumen 132 of the receiver 130 in the direction of arrow 812. When the implant associator 320 has passed back through the lumen 132, the implant 300 is free from the delivery device 100, and the wings 326a and 326b may then expand and resume their normal shape, width, and/or wingspan, wherein the concave shape of the wings prevents retrograde movement of the implant associator through the incision 530.

In certain embodiments, the mesh strap may have one or more non-tanged sections in the vicinity of the implant associator, such that transfer of the implant associator and a portion of the mesh strap may involve interaction of only non-tanged sections with the tissue, thereby facilitating passage of the implant through the tissue. The medical operator can then tighten or tension the implant by pulling additional lengths of the implant though the tissue, and these additional lengths may have one or more tanged sections. Such tanged sections may be pulled into the tissue, where they can facilitate anchoring of the mesh strap and/or promote tissue growth. Examples of implants including tanged and non-tanged sections and edges are described in U.S. Pat. No. 6,953,428, which is incorporated by reference herein, and are contemplated for use with the systems, methods, devices, and implants disclosed herein.

Figure 9:
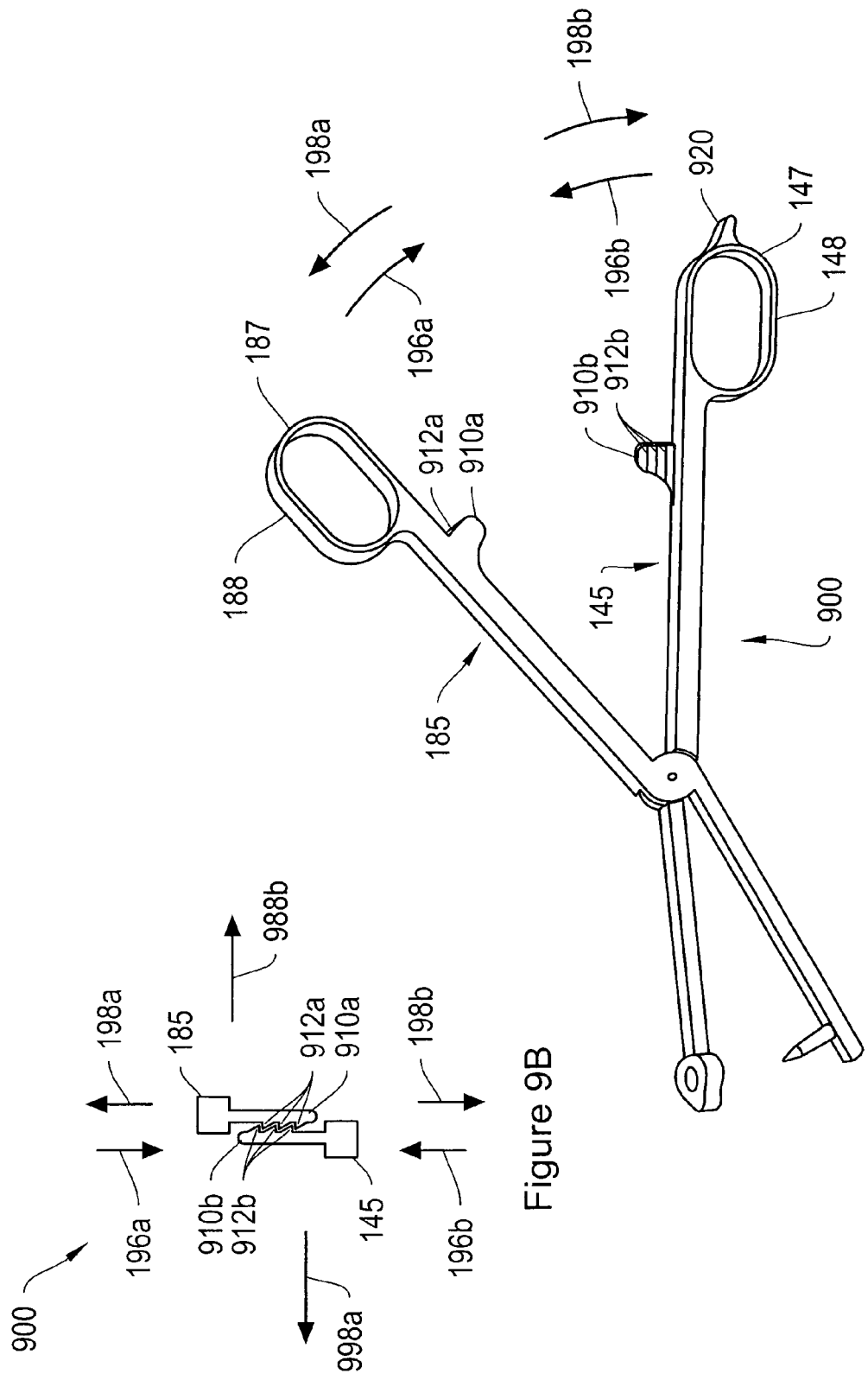
FIG. 9A depicts a delivery device including locking mechanisms according to an illustrative embodiment of the invention.
FIG. 9B depicts a cross-sectional view of a delivery device including locking mechanisms according to an illustrative embodiment of the invention.

FIG. 9A depicts a delivery device 900 according to another illustrative embodiment of the invention. The delivery device 900 includes many of the same features as the delivery device 100 and other devices described herein. Additionally, the delivery device 900 further includes locking mechanisms 910a and 910b disposed on the top handle section 185 and the bottom handle section 145, respectively. The locking mechanisms 910a and 910b each include complementary locking features 912a and 912b, respectively, which are stepwise bumps, ridges, and/or grooves. FIG. 9B depicts a cross-sectional view of the delivery device 900 at the site of the locking mechanisms 910a and 910b when the handles 148 and 188 are in a locked position. When the medical operator brings the handles 148 and 188 together in the direction of the arrows 196a and 196b, the locking features 912a and 912b slide over one another. Once the locking features 912a and 912b have slid over one another, the handles are "locked" and the delivery device 900 is locked in the closed position as retrograde movement of the locking features in the direction of the arrows 198a and 198b is prevented through abutment of the locking features with one another. When the handles are locked, the delivery device can remain in the closed position indefinitely unless subject to further manipulation by the medical operator. The medical operator may "unlock" the handles 148 and 188 and open the delivery device 900 by temporarily separating the top handle section 185 and the bottom handle section 145 in the direction of the arrows 998a and 998b, thereby removing the abutment of the locking features 912a and 912b and permitting movement of the handles in the direction of the arrows 198a and 198b. Although the locking mechanisms 910a and 910b are depicted distal to the handles 148 and 188, relative to the proximal ends 147 and 187, respectively, the locking mechanisms may be placed at a more proximal location, for example, near or at the handles or near or at the proximal ends 147 and 187. Additionally, other means for locking the handles 148 and 188 are contemplated including clips, fasteners, adhesives, elastic bands, springs, etc.

The delivery device 900 of FIG. 9A further includes an optional extension 920 on the handle 148. The extension 920, which may be on one or both of the handles 148 and 188, may provide an additional point of leverage and/or gripping by one or more fingers of the medical operator when grasping the device 900.

Figure 10:
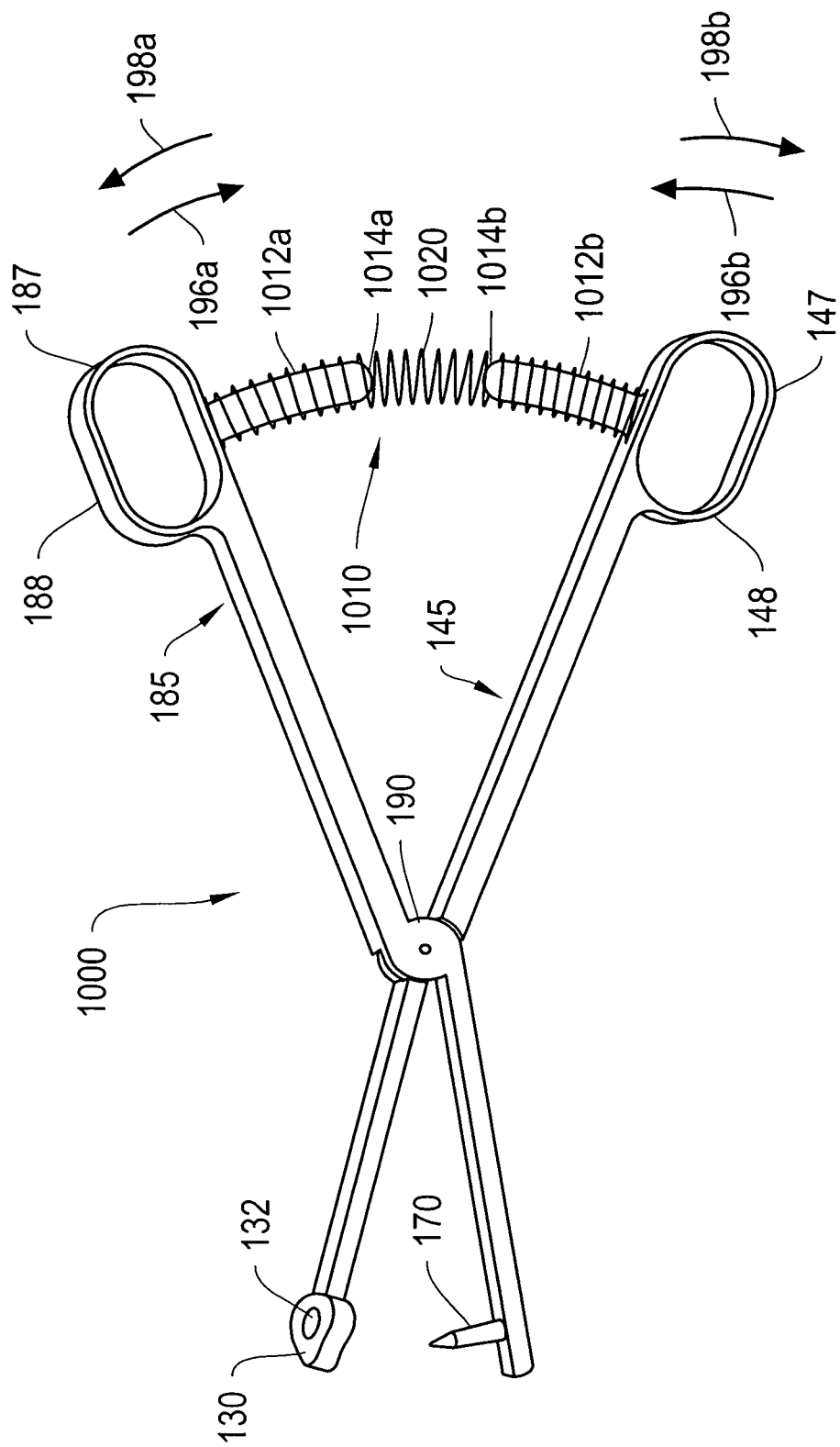
FIG. 10 depicts a delivery device including a separating mechanism according to an illustrative embodiment of the invention.

FIG. 10 depicts a delivery device 1000 according to another illustrative embodiment of the invention. The delivery device 1000 includes many of the same features as the delivery device 100 and other devices described herein. Additionally, the delivery device 1000 includes separating mechanism 1010, which resiliently urges the top handle section 185 and the bottom handle section 145 apart and permits the delivery device to remain in the open position indefinitely unless subject to further manipulation by the medical operator. The separating mechanism includes two bumpers 1012a and 1012b which project toward one another from the top handle section 185 and the bottom handle section 145, respectively. The bumpers 1012a and 1012b are associated by a spring 1020 which may surround and/or connect the bumpers and which may also connect the top and bottom handle sections 185 and 145 at the handles 188 and 148, respectively. When the medical operator squeezes the handles 148 and 188 in the direction of the arrows 196a and 196b, the spring 1020 is compressed, providing resistance to the squeezing. On continued squeezing, the bumpers 1012a and 1012b come together and contact at their tips 1014a and 1014b, respectively. The contact of the tips 1014a and 1014b prevents further squeezing of the handles, and the delivery device 1010 is in a partially closed or partially open position. If the medical operator releases the squeezing pressure, the spring 1020 can separate the handles 148 and 188 in the direction of the arrows 198a and 198b and reopen the delivery device 1010. Accordingly, the degree of closure of the delivery device 1000 is determined by the point of contact between the tips 1014a and 1014b. The point of contact can be varied by varying the length of the bumpers 1012a and 1012b. Shorter bumpers may permit increased closure of the delivery device and result in further penetration of the transfer pin 170 into tissue and/or into the lumen 132 of the receiver 130.

The spring 1020 may also facilitate opening of the delivery device 1000, particularly when opening may be hindered by retrograde passage of the transfer pin 170 through tissue. Furthermore, the spring 1020 may slow the progress of closure of the delivery device 1000, thus slowing the advancement of the transfer pin 170 through tissue and into the lumen 130. This may be advantageous when the medical operator desires penetrating soft, tender, or sensitive tissue for which careful, precise, or slow penetration is desired.

With continued reference to FIG. 10, although the bumpers 1012a and 1012b and the spring 1020 are depicted approximately equal with handles 148 and 188, relative to the proximal ends 147 and 187, respectively, the bumpers and the spring may be placed at a more proximal location, for example, near or at the distal ends, or at a more distal location, for example closer to the center portion 190, such as distal to the handles.

Figure 11:
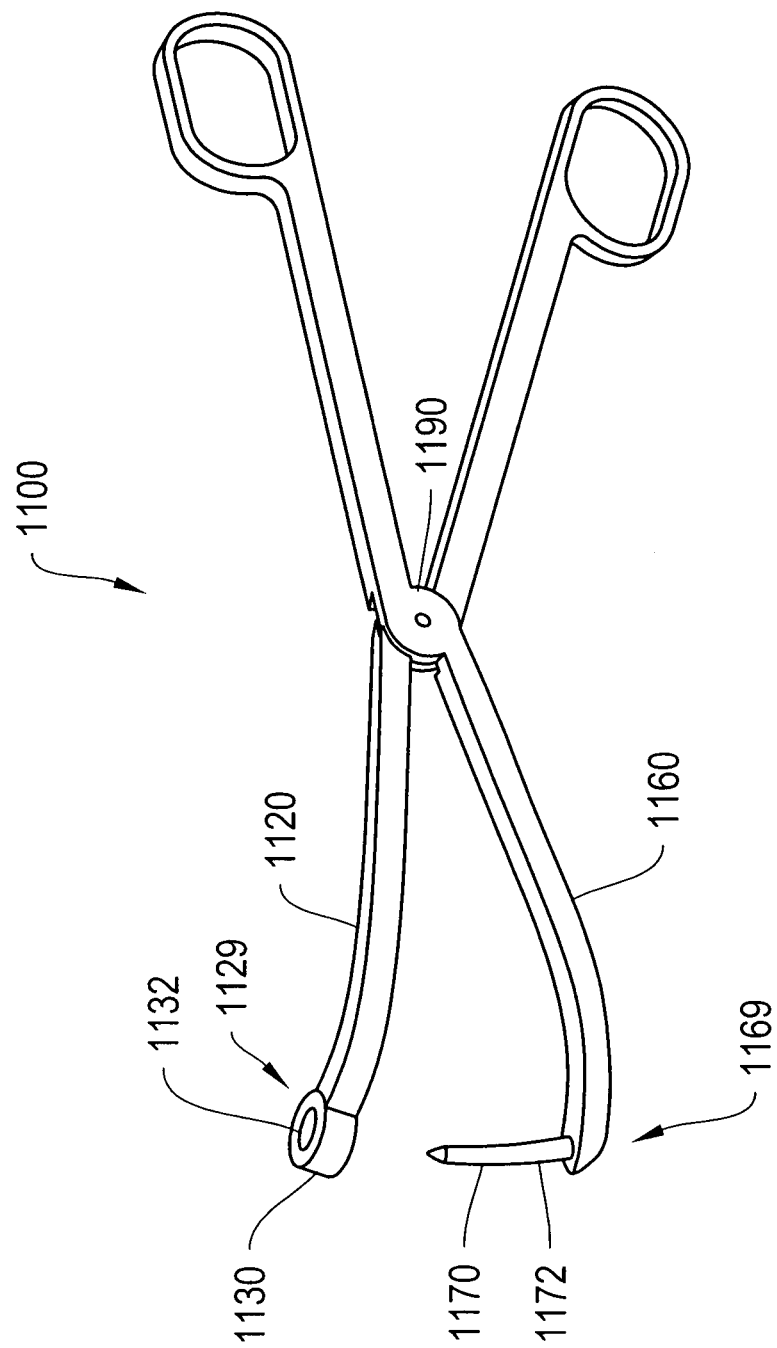
FIG. 11 depicts a delivery device including curved top and bottom sections according to an illustrative embodiment of the invention.

FIG. 11 depicts a delivery device 1100 according to another illustrative embodiment of the invention. In addition to including many of the same features as the delivery device 100 and other delivery devices disclosed herein, the device 1100 further includes matching curved top and bottom sections 1120 and 1160, respectively. The top and bottom sections 1120 and 1160 may curve continuously along their distal progression from the center portion 1190 or may increase or decrease (not shown) in curvature on approaching distal portions 1129 and 1169 respectively. The transfer pin 1170 may also be curved to facilitate progression into the lumen 1132 of the receiver 1130 and/or to facilitate tissue penetration. Alternatively, the transfer pin 1170 may be straight or substantially straight. As illustrated, the bottom section 1160 curves toward the top section 1120 on distal progression from the center portion. In other embodiments, the top section may curve toward the bottom section on distal progression from the center portion. Moreover, the top and bottom sections may include more than one region of curvature, for example curving in one direction followed by another direction optionally with one or more non-curved portions interspersed therein. The delivery devices disclosed herein may utilize different curvatures to facilitate delivery of implants to different anatomical sites in the patient. For example, the delivery device 1100 may allow for easier access and positioning of the device next to the tendinous arch of the levator ani muscle or "white line" and may facilitate delivery of a mesh strap through the tendinous arch of the levator ani muscle. In one embodiment, the delivery device 1100 is associated with an implant with an implant associator as described herein, is in the open position, and is positioned near the white line before being torqued to drive the transfer pin 1170 and an implant associated therewith into and out of the white line. The delivery device 1100 is subsequently closed to transfer the implant from the bottom section 1160 to the top section 1120.

Figure 12:
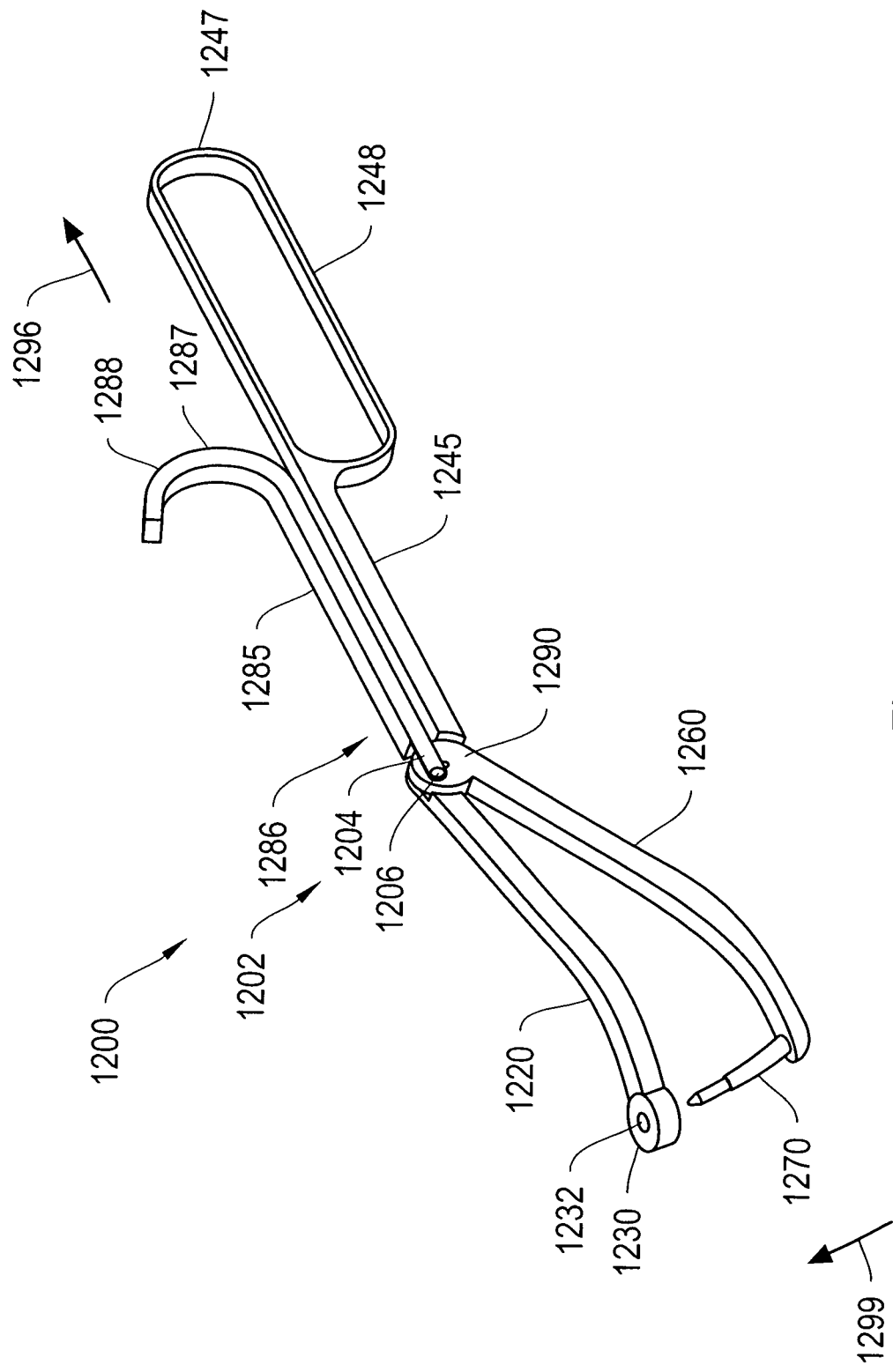
FIG. 12 depicts a delivery device including a cam system according to an illustrative embodiment of the invention.

FIG. 12 depicts a delivery device 1200 according to another illustrative embodiment of the invention. The delivery device 1200 includes a top section 1220, a bottom section 1260, a top handle section 1285, and a bottom handle section 1245. The bottom handle section 1245 includes a handle 1248 located at or near a proximal end 1247, and the top handle section 1285 includes a handle 1288, located at or near a proximal end 1287. The bottom section 1260 includes a transfer pin 1270, and the top section 1220 includes a receiver 1230 with a lumen 1232 for receiving the transfer pin. The delivery device 1200 further includes a cam system 1202 comprising a rod 1204 located at a distal end 1286 of the top handle section 1285. The rod 1204 is connected to a pin 1206 which attaches to a center portion 1290. The cam system 1202 operatively associates the top section 1220 and the bottom section 1260. In operation, the medical operator grasps the delivery device 1200 via the handles 1248 and 1288 and closes the delivery device by pulling on the handle 1288 in the direction of the arrow 1296. The pulling action causes the rod 1204 to pull on the pin 1206, which rotates the center portion 1290 such that the bottom section 1260 moves in the direction of the arrow 1299, and the transfer pin 1270 eventually enters into the lumen 1232 of the receiver 1230, optionally passing through any intervening tissue. The cam system 1202 may be used in place of the pivot system 102 of the delivery device 100 of FIG. 1, for example, if space considerations make expansion of the handles 148 and 188 inconvenient or difficult.

Figure 13:
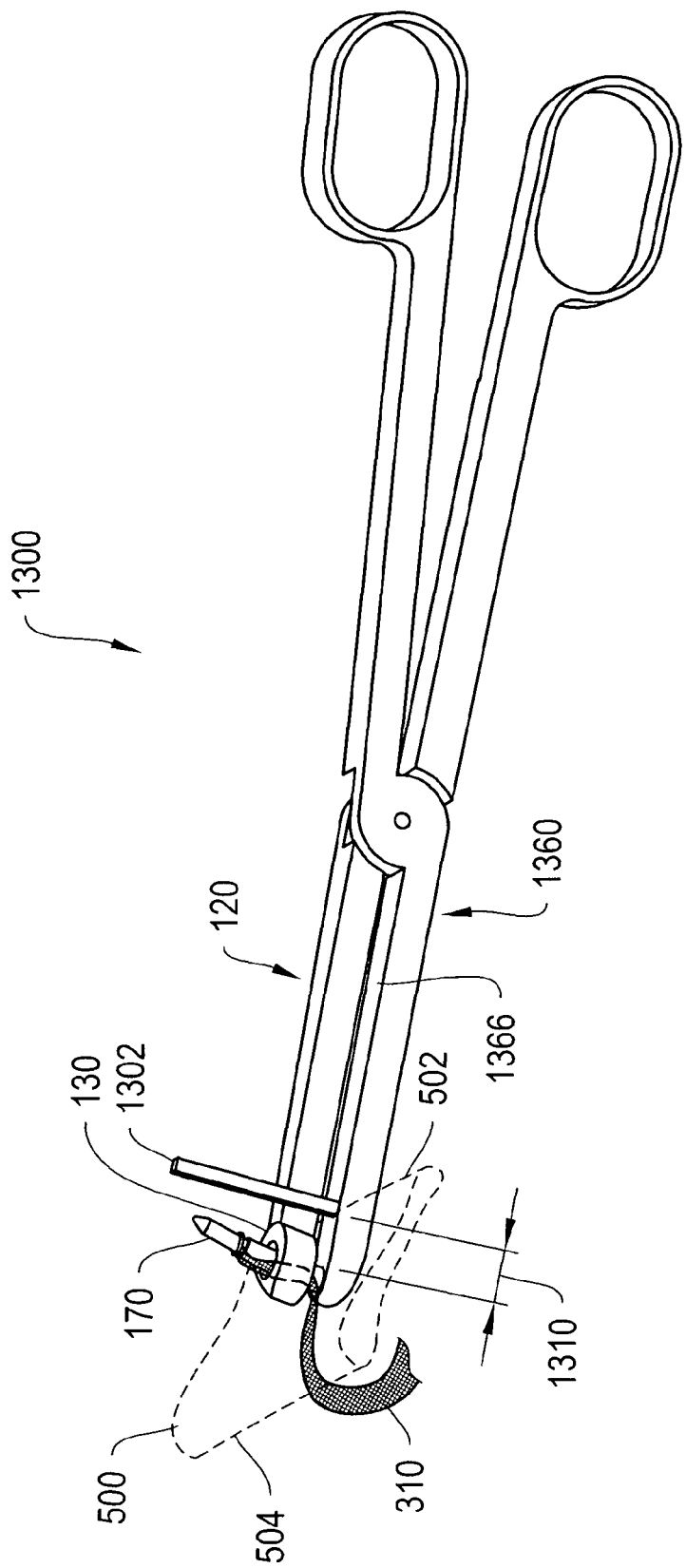
FIG. 13 depicts a delivery device including a stopper according to an illustrative embodiment of the invention.

FIG. 13 depicts a delivery device 1300 according to another illustrative embodiment of the invention. The delivery device 1300 includes many of the same features as the delivery device 100 and other delivery devices disclosed herein and also includes a stopper 1302, which protrudes from the top surface 1366 of the bottom section 1360. The stopper 1302 is spaced a reference distance 1310 from the transfer pin 170. When the bottom section 1360 and the top section 120 are placed around the tissue 500, the proximal side of the tissue 502 advances proximally until it abuts the stopper 1302. As such, when the medical operator drives the transfer pin 170 through the tissue 500, the transfer pin penetrates through the tissue a reference distance 1310 from the proximal side 502. The stopper 1310 allows the medical operator to accurately deliver the implant 310 to the tissue 500 a reference distance 1310 from the proximal end 502 of the tissue. Furthermore, the stopper 1310 prevents the medical operator from unintentionally penetrating the tissue 500 a distance from the proximal end 502 greater than the reference distance 1310, for example, preventing penetration adjacent to the distal side 504 of the tissue. The stopper 1310 also hinders the medical operator from unintentionally closing the delivery device 1300 when the transfer pin has advanced beyond the distal side 504 of the tissue. In some embodiments, the stopper is located at the top section 120 and projects from the bottom surface 128 (not shown) thereof. In other embodiments, more than one stopper is employed, for example, one on each of the top and bottom sections 120 and 1360. The receiver 130 may be positioned as necessary, for example, offset from the longitudinal axis of the top section 120, to ensure mating with the transfer pin 170.

Figure 14:
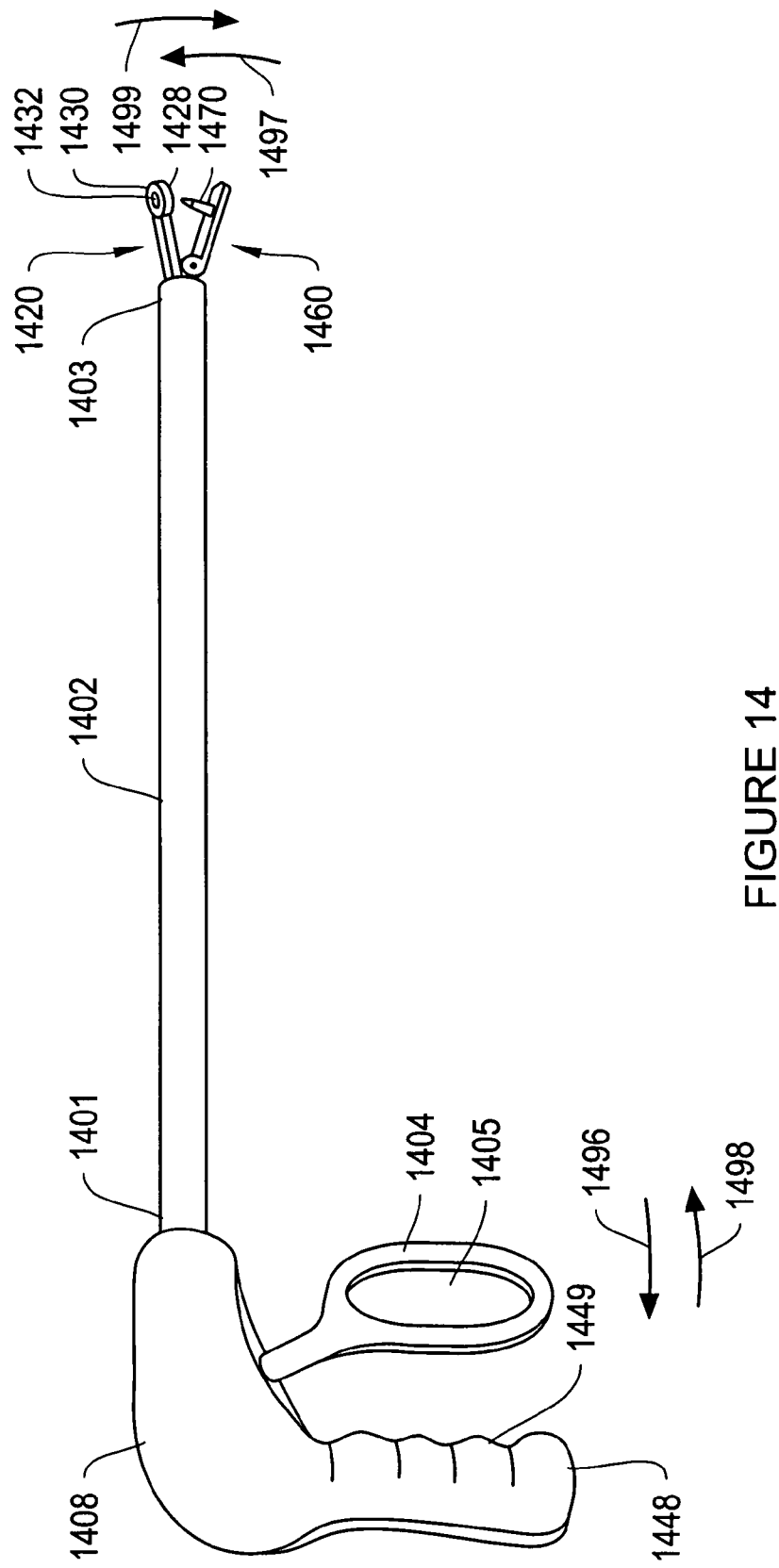
FIG. 14 depicts a delivery device according to an alternate illustrative embodiment of the invention.

FIG. 14 depicts a delivery device 1400 according to another illustrative embodiment of the invention. The delivery device 1400 includes a housing 1408 and a cannula or shaft 1402 projecting therefrom. The shaft includes a proximal end 1401 and a distal end 1403. Extending from the distal end 1403 is a bottom section 1460 including a transfer pin 1470. Also extending from the distal end 1403 is a top section 1420 with a bottom surface 1428 and a receiver 1430 including a through-lumen 1432 sized and shaped for receiving a portion of the transfer pin 1470 therein. The housing 1408 further includes a handle 1448, which includes one or more optional gripping features 1449 such as contours, grippable surfaces, notches, grooves, etc. to facilitate grasping by a medical operator. A trigger 1404 extends from the housing 1408. The trigger 1404 includes an aperture 1405 and/or other gripping features 1449, such as contours, grippable surfaces, notches, grooves, etc. to facilitate grasping by a medical operator. In other embodiments, the trigger does not include an aperture. In operation, the medical operator grasps the delivery device 1400 by the handle 1448 and pulls the trigger 1404 in the direction of the arrow 1496 with one or more fingers. Pulling of the trigger 1404 in the direction of the arrow 1496 closes the delivery device, for example, by a cam system (not shown) or pivot system (not shown), or other mechanism which may be located in the housing, as the transfer pin moves in the direction of the arrow 1497 and enters the lumen 1432 from the bottom side 1428. When the medical operator releases the trigger 1404, the delivery device 1400 may open as a spring action causes the trigger 1404 to return to an initial position in the direction of the arrow 1498, and the transfer pin 1470 moves in the direction of the arrow 1499 and exits the lumen 1432 from the bottom side 1428. The delivery device 1400 may be employed in situations where the medical operator desires extended reach by the transfer pin and receiver. The delivery device 1400 may also be used in laparoscopic applications where the medical operator desires viewing of internal tissues of the patient.

Figure 15:
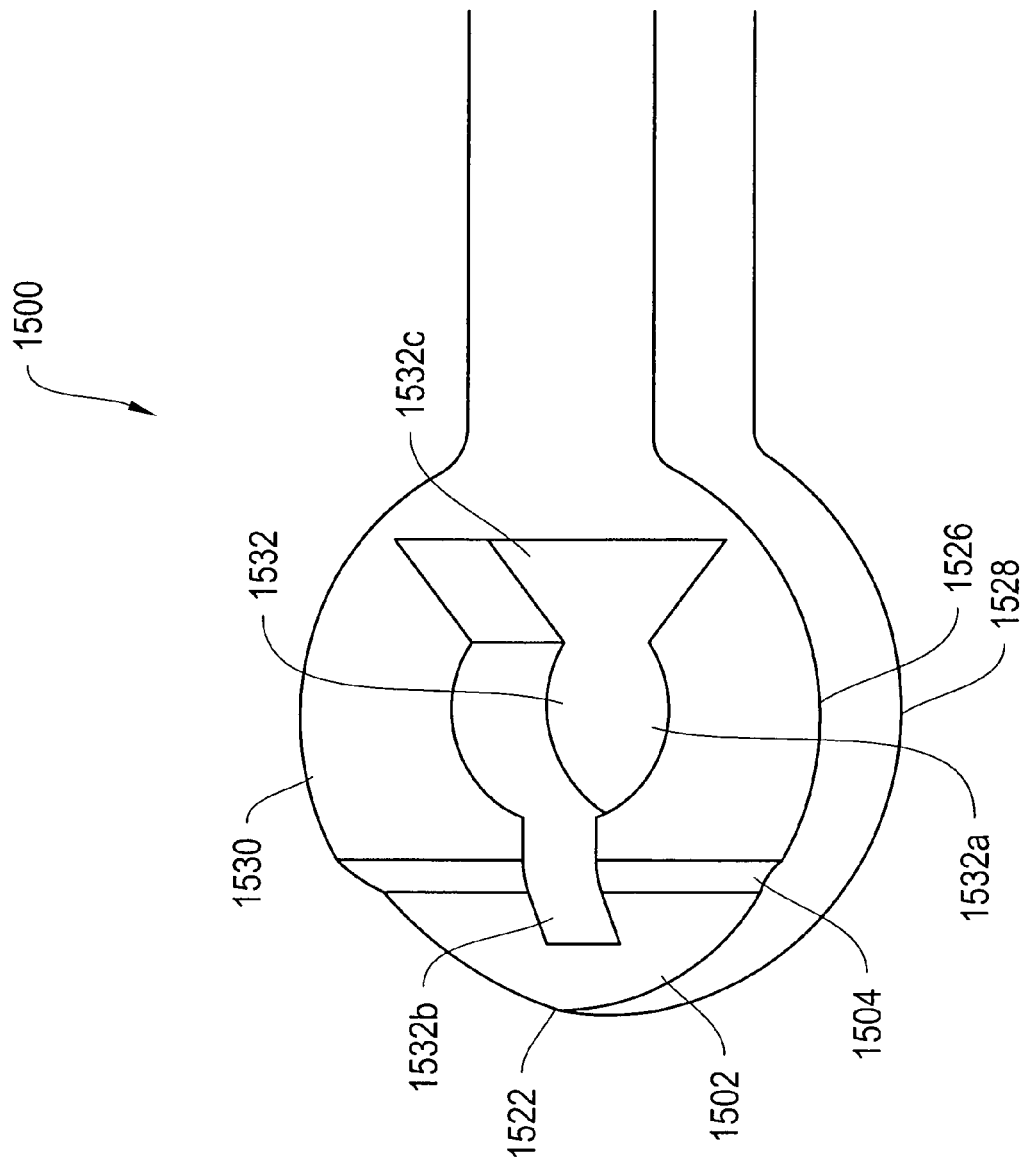
FIG. 15 depicts a receiver with lumen comprising a narrow notch and a wide notch according to an illustrative embodiment of the invention.

FIG. 15 depicts a receiver 1530 of a delivery device 1500 according to another embodiment of the invention. The receiver 1530 and variations thereof may be used with any devices disclosed or incorporated by reference herein. The receiver 1530 has a top surface 1526, a bottom surface 1528, and a lumen 1532. The receiver 1530 includes at a distal end 1522 an optional sloped surface 1502, which may facilitate insertion of the receiver 1530 into the tissues of a patient. The receiver 1530 may be sloped in the direction of tissue penetration, i.e., toward the distal end 1522 and the bottom surface 1528. The sloping may be continuous or it may be stepwise, for example, including one or more steps 1504. The lumen 1532 includes a circular portion 1532a, an optional narrow slot or notch 1532b, and an optional wide slot or notch 1532c. The narrow notch 1532b may be sized and shaped to hold a mesh strap and/or to allow a mesh strap to pass through. The narrow 1532b notch may also be sized and shaped to prevent an implant associator from passing from the top surface 1526 to the bottom surface 1528, for example, after the implant associator has been transferred from a transfer pin via the circular portion 1532a. The lumen 1532 may also include one or more additional notches in addition to the narrow notch 1532b and/or the wide notch 1532c. As described above, once the medical operator has transferred an implant associator and a mesh strap to the top surface 1526, the medical operator can tension the implant by pulling on the mesh strap by pulling on the receiver 1530. The mesh strap may slide into the narrow notch 1532b further securing the mesh strap during tensioning of the implant as the implant associator is prevented from passing through the narrow notch 1532b and the lumen 1532. The narrow notch 1532b may be sized and shaped as necessary, for example, having a circular, square, triangular, rectangular, oval, star, pentagonal, hexagonal, octagonal, polygonal, or other shapes.

As illustrated, the lumen 1532 includes a wide notch 1532c which may be sized and shaped to permit an implant associator and mesh strap associated thereto to pass from the top surface 1526 to the bottom surface 1528 or from the bottom surface to the top surface. For example, the wide notch 1532c may be sized and shaped to allow an implant associator, including wings, to fit through, optionally with assistance from a medical operator who may twist, bend, or temporarily deform the implant associator, if necessary. The wide notch 1532c may have a similar shape as the profile made by the wings or wingspan thereof of an implant associator. As such, the wide notch 1532c may be sized and shaped as necessary, for example, having a circular, square, triangular, rectangular, oval, star, pentagonal, hexagonal, octagonal, polygonal, or other shapes.

Figure 16A:
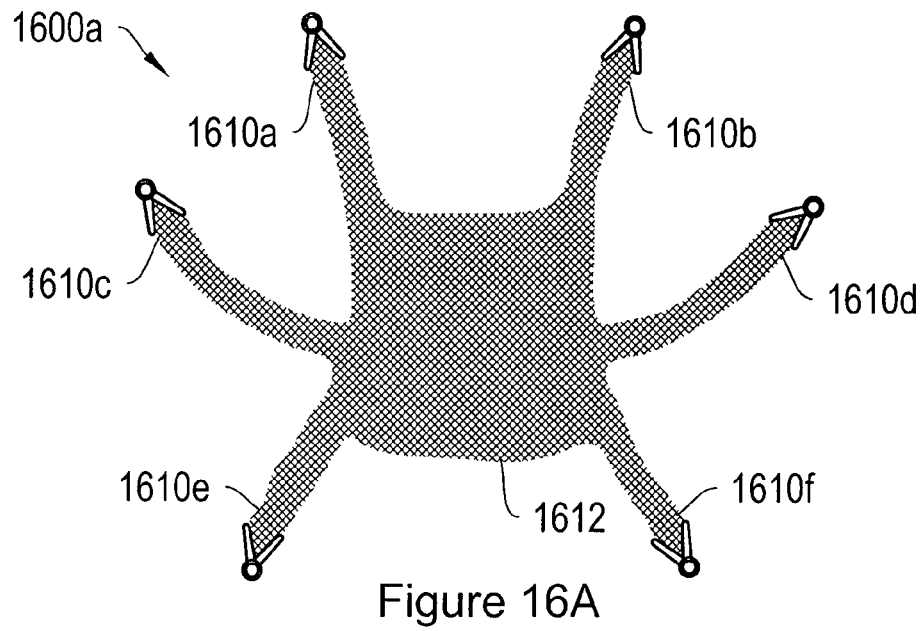
FIGS. 16A-F depict variations of implants according to illustrative embodiments of the invention.

FIG. 16A depicts an illustrative embodiment of an implant 1600a for use with the systems, devices, and methods described herein. The implant 1600a includes a plurality of extensions or mesh straps 1610a-f, similar to mesh strap 310, and central portion 1612. The plurality of extensions may be used to place the implant by securing or attaching one or more extensions to tissue at an anatomical site in a patient. The central portion 1612 may be placed under a portion of the patient's anatomy that requires support. The implant 1600a includes two anterior straps 1610a and 1610b and four posterior straps 1610c-f. While the depicted implant 1600a includes 6 straps, more or fewer straps can be used depending on the nature of the condition being treated, and exemplary embodiments include 2, 3, 4, 5, 7, 8, 9, 10, 11, 12, or more straps. For example, if a medical operator determines that a patient requires posterior support but not anterior support, an implant may comprise the four straps 1610c-f but not the two straps 1610a-b. The implant 1600a is described in operation in further detail below.

Figure 16B:
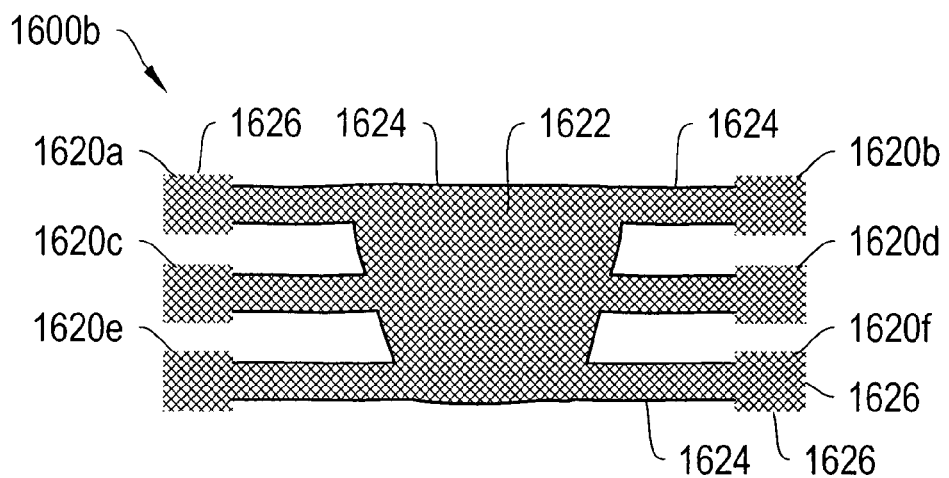
Figure 16C:
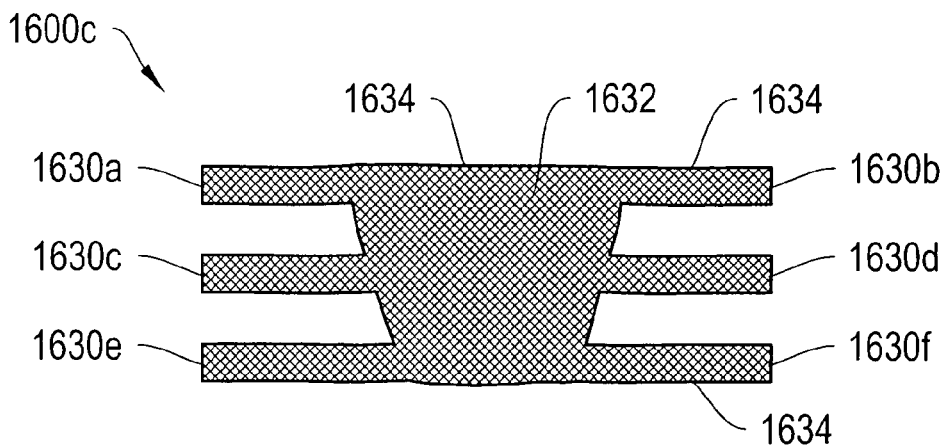

FIG. 16B depicts an illustrative embodiment of an implant 1600b. The implant 1600b includes a plurality of extensions or mesh straps 1620a-f and a trapezoidal central portion 1622. As noted above for the implant 1600a, one or more mesh straps 1620a-f may not be used depending on the needs of the patient. Although the mesh straps 1620a-f are shown to have tanged edges 1626 at terminal portions, in some embodiments, one or more of the mesh straps may have non-tanged edges 1624 at terminal portions. For example, FIG. 16C depicts an implant 1600c comprising a plurality of extensions or mesh straps 1630a-f and a trapezoidal central portion 1632. The mesh straps 1630a-f are shown to have non-tanged edges 1634 at terminal portions. In addition to trapezoidal, other shapes for central portions of implants, such as 1600a and 1600b-c, are contemplated, for example, circular, square, triangular, rectangular, oval, star-shaped, pentagonal, hexagonal, octagonal, polygonal, etc. In certain embodiments, central portions of implants have non-tanged edges, such as 1624 and 1634, which may reduce irritation or damage to the portion of the patient's anatomy in need of support. In some embodiments, extension and/or terminal ends of extensions may have one or more tanged edges, such as 1624, to improve securing with tissue and to encourage tissue growth.

Figure 16D:
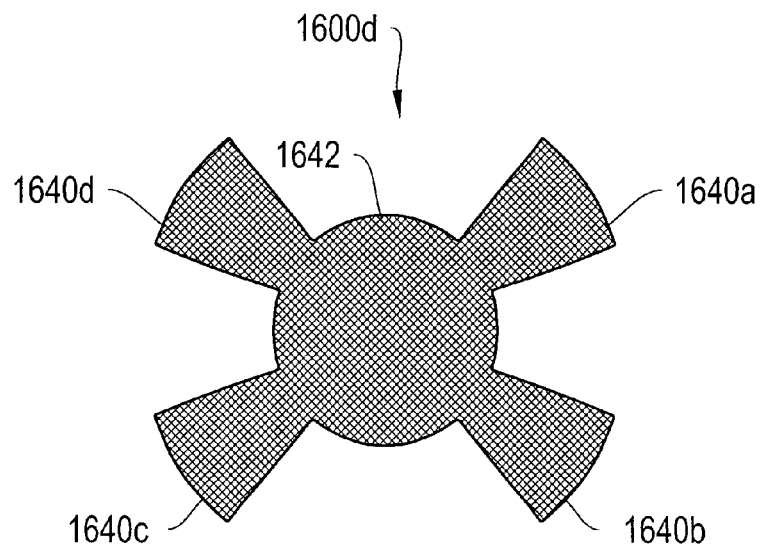

As noted above, implants with various numbers of extensions or straps may be employed. For example, FIG. 16D depicts an illustrative embodiment of the implant 1600d, which includes 4 extensions or mesh straps 1640a-d and a circular central portion 1642.

Figure 16E:
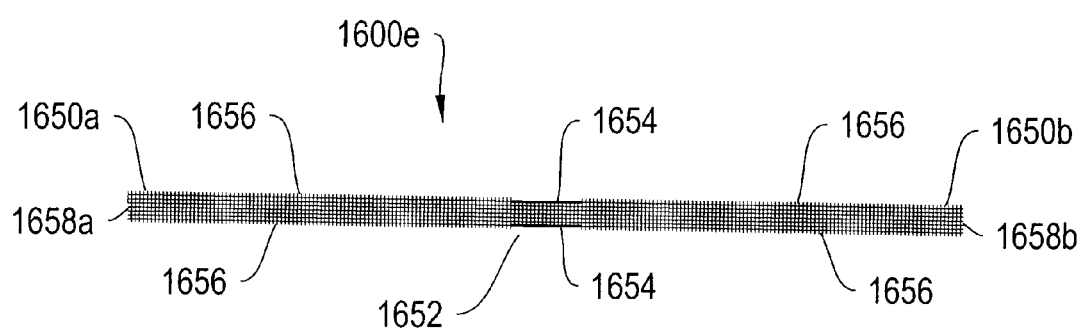
Figure 16F:
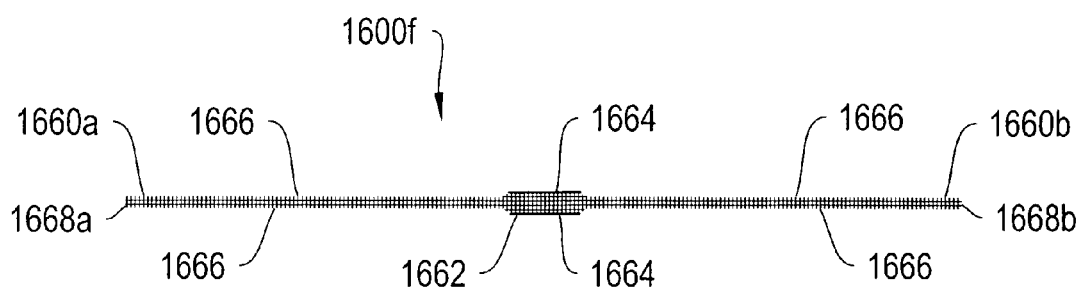

FIG. 16E depicts another embodiment of an implant, wherein the implant or sling 1600e includes two straps 1650a and 1650b and a central portion 1652. In the illustrated embodiment, the straps 1650a and 1650b include tanged edges 1656 along the majority of their length, including near and/or at the ends 1658a and 1658b. Moreover, the central portion 1652 includes non-tanged edges 1654, although a central portion with one or more tanged edges is also possible. Other embodiments include other combinations of tanged and non-tanged portions. For example, the straps and/or the central portion may include one or more alternating tanged and non-tanged portions. Similarly, FIG. 16F depicts another example of an implant, wherein the implant or sling 1600f includes two straps 1660a and 1660b with ends 1668a and 1668b and a central portion 1662. The straps 1660a and 1660b include tanged edges 1666, and the central portion includes non-tanged edges 1664. In the illustrated embodiment of FIG. 16F, the central portion 1662 is wider than the straps 1660a and 1660b; this may facilitate implantation of the straps when a reduced amount of tissue contact with the straps is desired. Additionally, this configuration may be applicable when an increased amount of support of the patient's anatomy by the central portion is desired. In other embodiments, such as that shown in FIG. 16E, the width of the straps and the central portion may be substantially similar. In further embodiments, the straps may be wider than the central portion.

As noted previously herein, implants such as implants 1600a-f, particularly, the implants 1600e-f, may include a protective pouch or envelope, enclosing or covering, either completely or at least partially, the implant, mesh strap, or sling. The envelope may include one or more sections, optionally distinct or coupled, which cooperate to enclose or cover the implant, mesh strap, or sling. For example, the envelope may have two sections or sleeves that cooperate to enclose or cover, either completely or at least partially, the implant, mesh strap, or sling.

Although the embodiments depicted in FIGS. 16A-F generally illustrate the straps for a given implant as having similar widths and lengths, one or more straps for a given implant may have different widths and/or lengths relative to another strap as necessary for improved securing within the tissues of the patient.

The illustrative embodiments discussed above illustrate devices and methods for securing an implant via an extension or mesh strap, such as 310, to a target tissue, such as a muscle or a ligament. As mentioned above, the mesh strap 310 can be a portion of a larger surgical implant, such as those depicted in FIGS. 16A-F, which can be used for pelvic floor support and/or repair.

Figure 17:
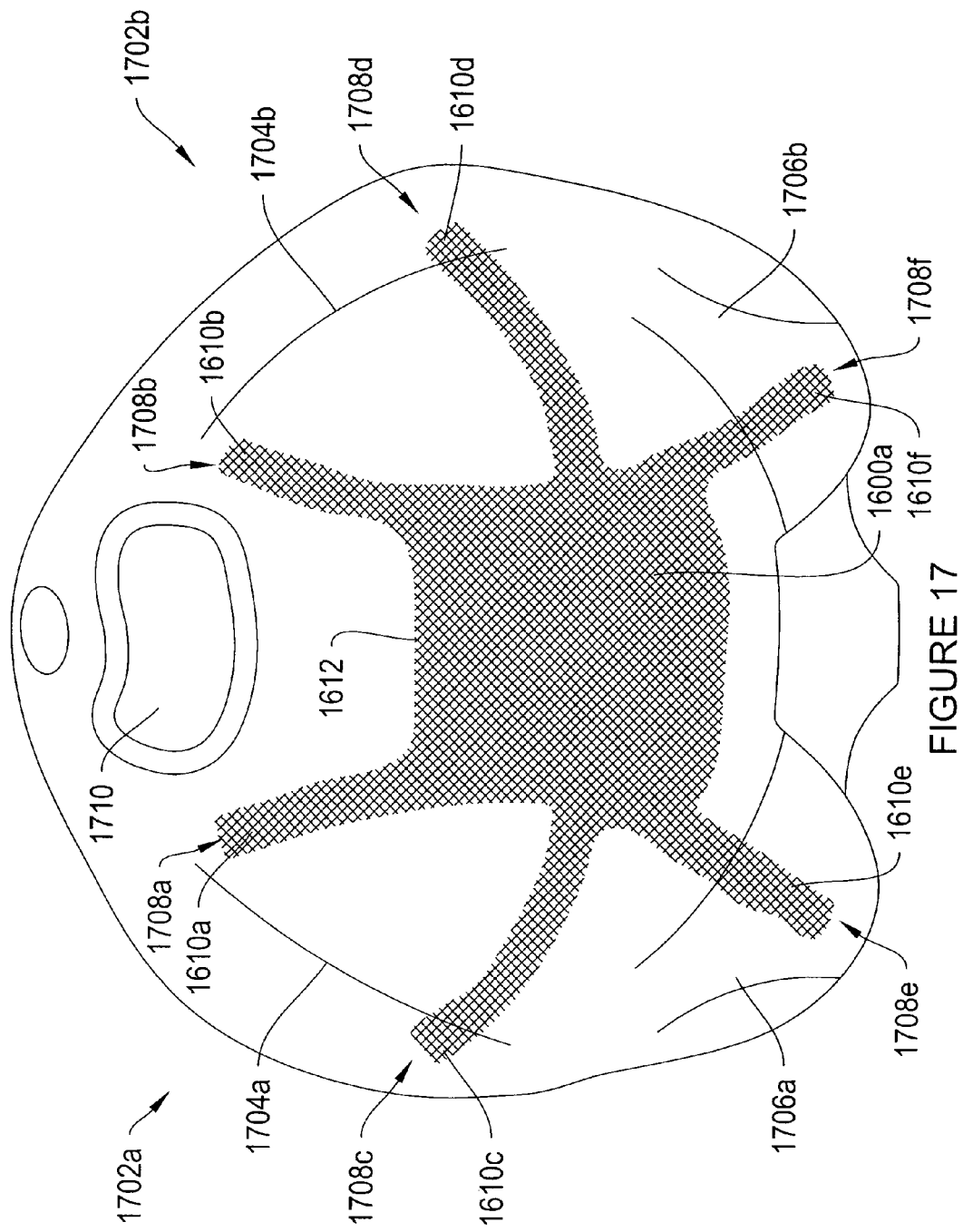
FIG. 17 depicts an inferior view of an implant implanted within a patient using a device according to an illustrative embodiment of the invention.

FIG. 17 depicts an inferior view of a pelvic floor implant 1600a positioned within a patient by the use of one or more of the devices described or referenced herein. As shown, the implant 1600a includes a central portion or region 1612 and a plurality of straps 1610a-f similar to mesh strap 310. The straps 1610a-f include two anterior straps 1610a and 1610b, and four posterior straps, 1610c and 1610e on one side, and 1610d and 1610f on the contra-lateral side.

Referring to FIG. 17, the mesh implant 1600a is sized and shaped to fit on or near the pelvic floor and support the bladder, the vagina, uterine artery, urethra, and/or the rectum. The straps 1610a-f are spaced apart so as to align with particular anatomical sites within the pelvic region for securing the implant 1600a thereto. As shown, the anterior straps 1610a and 1610b are positioned to align with the patient's obturator foramen (not shown, but generally located at regions 1702a and 1702b) and optionally can ultimately be pushed or driven through the patient's obturator membranes. Posterior straps 1610c and 1610d are positioned to align with the tendinous arch of the levator ani muscles 1704a and 1704b, and posterior straps 1610e and 1610f are positioned to align with the sacrospinous ligaments 1706a and 1706b. The mesh straps 1610a-f may be introduced in association with a delivery device described herein via the vaginal opening 1710 and/or one or more vaginal incisions (not shown) and be secured to tissue in target areas 1708a-f, respectively. The mesh straps 1610a-f may include features of extensions and/or mesh straps described herein, for example, including respective implant associators (not shown), similar to the implant associator 320 or others described herein.

The present disclosure further contemplates systems, kits, and delivery assemblies comprising one or more of devices, implants, and/or implant associators as described herein. For example, a kit may comprise 1, 2, 3, 4, 5, 6, 7, 8, or more delivery devices; 1, 2, 3, or more implants; and/or 1, 2, 3, 4, 5, 6, 7, 8, or more implant associators as described herein. The present disclosure further contemplates kits including devices and implants disclosed in references cited and incorporated by reference herein.

Delivery methods for implants compatible and contemplated with implants and delivery devices disclosed and referenced herein include, suprapubic, prepubic, transvaginal, transobturator, and other methods. Additional disclosure of such methods can be found in references cited and incorporated by reference herein.

In some embodiments, the delivery devices and/or delivery assemblies described herein are made of biocompatible materials, which can include, for example, poly-alpha-hydroxy acids (e.g. polylactides, polyglycolides and their copolymers), polyanhydrides, polyorthoesters, segmented block copolymers of polyethylene glycol and polybutylene terephtalate (Polyactive™), tyrosine derivative polymers or poly (ester-amides), polyethylene/ethylene vinyl acetate (EVA) blend, polyethylene, polyester, nylon, polypropylene, thermoplastic fluorinated ethylene propylene (FEP), TFP, stainless steel, malleable metal or any combination of these materials. In some embodiments, a delivery device described herein includes one or more components, such as a receiver or a transfer pin, that are formed of surgical grade stainless steel.

As mentioned above, the surgical implants described herein, such as implants 300 and 1600a-f of FIGS. 3 and 16A-F, are often comprise a mesh material. There are many suitable mesh materials, and the implant may be made of one or more different types of materials. Exemplary mesh materials include, for example, synthetic materials, natural materials (e.g., biological) or a combination thereof. The mesh may be fabricated from any of a number of biocompatible materials, such as nylon, silicone, polyethylene, polyester, polyethylene, polyimide, polyurethane, polypropylene, fluoropolymers, copolymers thereof, combinations thereof, or other suitable synthetic material(s). The material may be, for example, a biodegradable synthetic material. The term "biodegradable," as used herein, refers to the property of a material that dissolves in the body. Such materials may also be absorbed into the body, i.e., bioabsorbable.

Suitable bioabsorbable synthetic materials include, without limitation, polylactic acid (PLA), polyglycolic acid (PGA), poly-L-lactic acid (PLLA), human dermis and decellularized animal tissue. Human tissues may be derived, for example, from human cadaveric or engineered human tissue. Animal tissues may be derived, for example, from porcine, ovine, bovine, and equine tissue sources. The material may be an omnidirectional material, a material that has equivalent tensile strength from any direction, such as pericardium or dermis. Alternatively, the material may be an oriented material, a material that has a single direction where the tensile strength of the material is the highest. Oriented materials may include rectus fascia and/or facia lata, as well as oriented synthetic materials.

Exemplary biodegradable polymers, which may be used to form implants described herein also include, without limitation, polylactic acid, polyglycolic acid and copolymers and mixtures thereof, such as poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan, alginates and regenerate cellulose; poly(amino acid) and proteins, such as gelatin and collagen; and mixtures and copolymers thereof.

In some embodiments, the implant, either as a whole or on a fiber by fiber basis, may include one or more agents for release into the patient's tissues. One illustrative agent is a tissue growth factor that promotes, when applied to the patient's tissues in a pharmaceutically acceptable amount, well-organized collagenous tissue growth, such as scar tissue growth, preferably, in large quantities. According to one feature, the agent may or may not block or delay the dissolvability of the biodegradable materials. This may be controlled by selecting differing methods for loading the agent onto the implant. The tissue growth factor may include natural and/or recombinant proteins for stimulating a tissue response so that collagenous tissue such as scar tissue growth is enhanced. Exemplary growth factors that may be used include, but are not limited to, platelet-derived growth factor (PDGF), fibroblast growth factor (FGF), transforming growth factor-beta (TGF-beta), vascular endothelium growth factor (VEGF), Activin/TGF and sex steroid, bone marrow growth factor, growth hormone, Insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues. Besides applying active pharmaceutical agents, passive agents may be applied to promote tissue ingrowth. For example, titanium sputtering or chrome sputtering can be used.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenylbutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the slings described herein include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-ltrimethyl-3,3-diphenylpropylamine, tropenzile, trospium chloride, xenytropium bromide, and pharmaceutically acceptable salts thereof.

The present disclosure contemplates all combinations of features and elements disclosed herein. For example, various embodiments of delivery devices, transfer pins, implants, implant associators, and other features described herein are interchangeable with one another, unless explicitly stated otherwise. As such, combinations of these embodiments, if not explicitly disclosed, are contemplated and within the scope of the present disclosure.

The contents of all references, patents and published patent applications cited throughout this Application, as well as their associated figures are hereby incorporated by reference in entirety.

The Figures and drawings referred to herein are not necessarily to scale; emphasis instead is generally placed upon illustrating the principles of the illustrated embodiments.

Variations, modifications, and other implementations of what is described herein will occur to those of ordinary skill without departing from the spirit and the scope of the present disclosure. Hence, many equivalents to the specific systems, methods, and other embodiments described herein exist and are considered to be within the scope of the present disclosure. For additional illustrative features that may be used with the present disclosure, including the embodiments described here, refer to the documents listed herein above and incorporated by reference in their entirety. All operative combinations between the above described illustrative embodiments and those features described in the documents incorporated by reference herein are considered to be potentially patentable embodiments of the claimed invention.

What is claimed is:

1. A device for delivering, to an anatomical site in a patient, an implant including an implant associator having a ring, the device comprising:
    a first section having a rounded distal portion which narrows in a direction of tissue penetration, the first section including a receiver located at the distal portion of the first section, the receiver including a through-lumen;
    a second section including a transfer pin located at a distal portion of the second section, the transfer pin comprising a conical tip sized to fit within the ring of the implant associator, the second section being movable relative to the first section;

a shaft with a distal end and a proximal end, the first section and the second section being located adjacent the distal end of the shaft;

a housing located adjacent the proximal end of the shaft; and a trigger associated with the housing, the trigger being adapted to effect entry of the transfer pin into the through-lumen of the receiver, wherein the through-lumen is adapted to receive the transfer pin and the implant associator when the transfer pin is associated with the implant.

2. The device of claim 1, wherein the receiver includes a sloped surface.

3. The device of claim 1, wherein the through-lumen of the receiver is substantially cylindrical.

4. The device of claim 1, wherein a cross-sectional area of the through-lumen of the receiver varies along a length of the through-lumen.

5. The device of claim 1, wherein the through-lumen includes a notch.

6. The device of claim 1, wherein the through-lumen includes a first relatively narrow and a second relatively wide notch.

7. The device of claim 1, wherein the transfer pin is substantially straight.

8. The device of claim 1, wherein the transfer pin includes at least one curved section.

9. The device of claim 1, wherein the transfer pin includes a shaft and a terminal section including the conical tip.

10. The device of claim 9, wherein the shaft includes a relatively narrow section and a relatively wide section.

11. The device of claim 1, wherein the transfer pin includes a shoulder or at least one projection.

12. The device of claim 9, wherein the terminal section is substantially conical.

13. The device of claim 1, wherein the transfer pin is adapted to interfit within an aperture of the implant associator.

14. The device of claim 1, wherein the implant comprises a mesh strap or a sling.

15. The device of claim 14, wherein the implant includes a protective envelope at least partially enclosing the mesh strap or the sling.

16. The device of claim 15, wherein the envelope includes two sleeves that cooperate to at least partially enclose the mesh strap or the sling.

17. The device of claim 1, further comprising a separating mechanism for resiliently urging the first and second sections apart.

18. The device of claim 1, wherein at least one of the first and second sections includes at least one curved section.

19. The device of claim 1, further comprising a pivot system operatively connected between the first and second sections.

20. The device of claim 1, further comprising a cam system operatively connected between the first and second sections.

21. The device of claim 1, further comprising a stopper connected to at least one of the first and second sections.

22. A system for delivering an implant to an anatomical site in a patient comprising:
a delivery device including:
first and second sections associated by a first hinge pin, the first section including a receiver having a through-lumen, the second section including a transfer pin comprising a conical tip adapted for associating with the implant; and
a trigger operatively coupled with the transfer pin such that actuation of the trigger effects entry of the transfer pin into the through-lumen of the receiver; and
the implant, including an implant associator having a ring and a plurality of wings extending away from the ring, the plurality of wings being configured to impede advancement, in at least one direction, of the implant associator through the through-lumen of the delivery device
wherein the transfer pin is adapted for associating with the ring of the implant associator, and the through-lumen is sized to permit the implant associator of the implant to pass through the through-lumen from a first side of the receiver to a second side of the receiver.

23. The system of claim 22, wherein the plurality of wings inhibit passage of the implant associator through the through lumen following passage of the associator from the first side to the second side.

24. The system of claim 22, wherein the implant includes at least one non-tanged edge.

25. The system of claim 22, wherein the implant further includes an extension, the implant associator being associated with the extension.

26. The system of claim 25, wherein the implant comprises 2, 4, or 6 extensions.

27. The system of claim 22, wherein the transfer pin includes a narrow portion sized to fit within the ring of the implant associator and a shoulder sized to prevent movement of the implant associator therepast.

28. The system of claim 27, wherein the shoulder is a circular step.

29. The system of claim 22, wherein the implant includes a protective envelope at least partially enclosing the implant.

30. The system of claim 22, wherein the anatomical site is the sacrospinous ligament or the tendinous arch of the levator ani muscle.

31. The system of claim 22, wherein the implant further includes a central portion configured to provide support to the anatomical site in the patient.

32. A method for transferring an implant having an implant associator including a ring from a second section of a delivery device to a first section of the delivery device, comprising:
associating the implant with a conical tip of a transfer pin of the second section, the implant including a protective envelope; and
closing the delivery device such that the transfer pin and the implant associator pass through a lumen of the first section from a first side of the first section to a second side of the first section, wherein the implant comprises a plurality of legs such that the implant can pass in one direction through the lumen but is impeded from passing in a second direction through the lumen.

33. The method of claim 32, further comprising transferring the implant through a tissue of a patient.

34. The method of claim 33, wherein the tissue is the sacrospinous ligament or the tendinous arch of the levator ani muscle.

35. A method for securing an implant having an implant associator including a ring to an anatomical site in a patient, comprising:
creating an incision in a pelvic region of the patient;
associating a conical tip of a second section of a delivery device with the ring of the implant associator;
inserting the delivery device and the implant into the patient via the incision to a location near the anatomical site, the implant including a protective envelope; and transferring the implant or a portion thereof from the second section of the delivery device, through tissue of the patient at the anatomical site, to a first section of the delivery device, wherein the first and second sections of the delivery device are associated by a first pin, and wherein transferring the implant or portion thereof includes passing the implant or portion thereof through a lumen of the second section from a first side of the second section to a second side of the second section.

36. The method of claim 35, further comprising removing the protective envelope.

37. The method of claim 35, wherein the incision is a vaginal incision.

38. The method of claim 35, wherein the tissue is the sacrospinous ligament or the tendinous arch of the levator ani muscle.

* * * * *